(12) United States Patent
Seex

(10) Patent No.: US 11,191,533 B2
(45) Date of Patent: Dec. 7, 2021

(54) RETRACTION ASSEMBLY FOR SURGERY

(71) Applicant: RETROSPINE Pty Ltd, Kingswood (AU)

(72) Inventor: Kevin Seex, Kingswood (AU)

(73) Assignee: RETROSPINE PTY LTD, Kingswood (AU)

( * ) Notice: Subject to any disclaimer, the term of this patent is extended or adjusted under 35 U.S.C. 154(b) by 0 days.

(21) Appl. No.: 15/959,924

(22) Filed: Apr. 23, 2018

(65) Prior Publication Data

US 2020/0205798 A1  Jul. 2, 2020

(30) Foreign Application Priority Data

Apr. 23, 2017 (AU) ................................ 2017901473

(51) Int. Cl.
*A61B 1/32* (2006.01)
*A61B 17/02* (2006.01)

(52) U.S. Cl.
CPC .. *A61B 17/0218* (2013.01); *A61B 2017/0225* (2013.01)

(58) Field of Classification Search
CPC combination set(s) only.
See application file for complete search history.

(56) References Cited

U.S. PATENT DOCUMENTS

| | | |
|---|---|---|
| 6,416,465 B2 | 7/2002 | Brau |
| 6,692,434 B2 | 2/2004 | Ritland |
| 2003/0014934 A1 | 1/2003 | Bodnar |
| 2005/0154395 A1 | 7/2005 | Robbins et al. |
| 2008/0008195 A1 | 1/2008 | Oberle et al. |
| 2012/0024543 A1 | 2/2012 | Head |
| 2015/0164569 A1* | 6/2015 | Reitblat ............ A61B 17/7079 606/279 |

* cited by examiner

*Primary Examiner* — Sameh R Boles
(74) *Attorney, Agent, or Firm* — Stephen J. Weyer; Stites & Harbison, PLLC

(57) ABSTRACT

A retraction assembly for use in retracting soft tissue during spine surgery having a reactor blade having a blade body and proximal and distal ends, a support member engagable with the blade body and having proximal and distal ends. The proximal end engages a passage in the blade body and the second end of the support member includes an anchorage capable of anchoring the assembly to an anatomical structure while allowing movement of the support member. The retractor blade is capable of detachable engagement with and movement relative to the support member. The retractor blade is capable of detachable engagement with and movement relative to the support member. The first end of the support member includes operating nuts to adjust the support member rotationally and vertically.

8 Claims, 33 Drawing Sheets

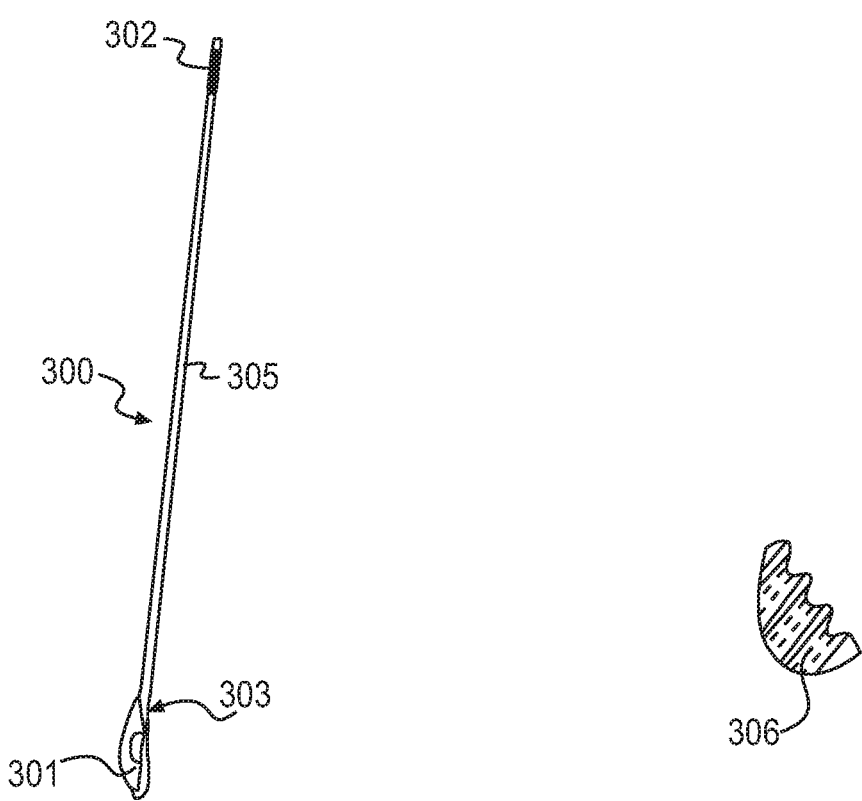
*FIG. 34e*   *FIG. 34f*

RETRACTION ASSEMBLY FOR SURGERY

BACKGROUND

The present invention relates to retraction assemblies used for retracting soft tissue in surgery and particularly spinal surgery and which allow optimal access to a surgical site. More particularly, the invention relates to a retracting assembly which includes a retractor blade, at least one support member for the blade and at least one anchor enabling engagement of the assembly with either soft tissue or bone. The invention further relates to a retraction assembly including a blade, an anchorage which engages vertebral bone and which includes a support member which receives and retains the blade during retraction. The invention further provides a retraction assembly including a support member for receiving and retaining a retractor blade and a formation at a distal end of the support which engages soft tissue or bone; the anchorage enabling the assembly and blade to move relative to the anchorage to thereby provide by manual adjustment or displacement, a clear path to a surgical site.

Although the invention is described below primarily in relation to spinal surgery, the principles and geometry embodied in the retractor blade assembly have alternative applications in which retraction of soft tissue is required along with capacity to adjust the attitude of the retractor blade to improve access to the surgical site and which can be anchored in soft tissue or bone.

PRIOR ART

There are in existence a number of assemblies used in retraction of soft tissues and which include retractor blades which engage bone during such retraction. In particular, there are known retractor blades and assemblies which retract soft tissue during spinal surgery. Such retractor blades are maintained at a setting to allow a surgeon access to a spinal disc space and vertebrae in cervical and lumbar spinal disc surgery.

Retractors are sometimes used in conjunction with distraction assemblies. The process of separating bones is termed distraction. This involves insertion of a spreading type instrument into an excised disc space which engages the upper and lower vertebral bodies and when applied separates them. This is known as intervertebral distraction. In the cervical spine, in a procedure known as non-intervertebral distraction may be used in which long screws are inserted into the upper and lower vertebral bodies and forces applied to spread screws and thus the bodies themselves. Surrounding soft tissues must be held apart by retractors. Once retracted, there is a natural elastic recoil of the stretched tissues so it is essential to employ retractors which effectively restrain soft tissues and without loosing the requisite retraction.

It is important to reduce trauma to soft tissues which may occur from contact with parts of retractor blades so that the surgical procedure is as minimally invasive as possible and thus minimally interferes with and minimally traumatizes the organs, tissues and vasculature being displaced while allowing access to the vertebral region being treated. Various types of retractors are known each having means to enable retention by a support member which usually retains a proximal end.

It is recognized by spinal surgeons that the most difficult and dangerous part of the surgery on the anterior lumbar disc spaces is dissection, mobilization and maintenance of retraction of the vessels, and in particular the left common iliac vein. Whatever level of surgery is being performed, there is an initial approach requiring some degree of soft tissue retraction. In the known art, the approach and surgery generally requires the use of handheld retractors, at least initially, which may then be replaced with fixed retractors to maintain retraction for the rest of the procedure.

Fixed retractors require either internal fixation to spinal vertebra or external fixation using a table mounted system. Retractors are usually positioned to hold tissues away from the surgical field both laterally (side to side) and longitudinally (up and down) relative to a spine. It is the lateral retraction that represents the greatest difficulty requiring a solution.

Existing retractors may be internally or externally fixed. Internal fixation of retractors is utilized to hold the left common iliac vein or other tissues in a retracted position. There is a danger that veins may be punctured or squeezed. Due to the difficulty and dangers of moving and keeping the blood vessels retracted during anterior lumbar surgery, stability of the retractors is particularly important. The most stable retractors are those embedded in the bone e.g. Steinman pins and Hohmann retractors. Steinman pins are long pins impacted into the bone while Hohmann retractors are conventional retractor blades with a curved pointed end which can be impacted into the bone for stability. Some limited movement of the Hohmann blade is possible by bending. Also known are standard retractor blades that have a channel that allow separate introduction of sharp pins through the channel into the vertebral body thus securing the blade to the spine.

There are numerous retraction assemblies available such as that disclosed in U.S. application 2003014934 which discloses a retractor anchored to bone and which is incorporated by reference herein. U.S. 2008008195 discloses an inflatable retractor anchored to a spine and U.S. 2012024543 discloses a disc anchor each incorporated by reference herein.

The aim of a retractor is to hold back soft tissue creating an access path for a surgeon to gain access to the surgical site. Adjustments are required to provide an access path but the available adjustment and extent of the adjustment allowed by the particular retraction assembly varies according to the nature and geometry of the retractor or retraction assembly. In some known assemblies, setting up and removal of the retraction assembly can risk soft tissue damage especially to vessels and nerves. Desirable attributes of a retraction blade or retraction blade assemblies are convenient insertion, ability to adjust through as many degrees of freedom as possible and allowing a clear and large enough path to the surgical site.

Internally fixed retractors have limitations and although very stable, once in place are not adjustable and insertion does produce bone injury. Insertion and removal can also be hazardous to vessels or other soft tissues. Anchoring into bone can also loosen under load especially when variable amounts of retraction are employed.

External fixation of retractors is achieved by the use of table mounted retractors. Various table mounted retractor systems are available e.g. Thomson, Omnitract, Bookwalter and Synframe. The table based systems offer a variety of retractor blades for holding back the tissues connected to a table mounted ring or support frame. Various shapes of blade are available. In order to improve on these and in particular to improve stability of these non internally fixed blades a new shape of retractor blade, called The Brau Blade, was developed. This blade is described in U.S. Pat. No. 6,416,465 incorporated by referenced herein. There are other blade assemblies in the prior art such as that disclosed in U.S. Pat. No. 6,692,434 and U.S. patent application No. 20050154395 incorporated by reference herein.

The Brau device is characterised in having a forward directed lip of the distal tip of the blade that curves forward away from the plane of the blade in an opposite direction to that of the handle, i.e. towards the spine. This has a gently curved point or blunt lip that contacts the side of the spine and provides more stability than alternative blades during insertion of the retractor and possibly maintenance of retraction. It also has ridges in the lip to increase purchase with the side of the vertebral body or disc.

Most conventional blades rely only on their external fixation for stability. If there is contact with the bone it lies at the side of the vertebral body usually at or above the equator of the vertebrae where the bone is curving posterolaterally. Contact and pressure on the blade against the bone improves stability of retractor blades. The lip of the Brau blades and all other conventional blades when used for lateral retraction are in contact with the bone along the side of the body. Many conventional blades sit beside the bone with a lip curving away from the bone. Despite sophisticated linkages of the blades to their handles and their handles to the frame, it is mechanically difficult to keep blades immobile. Once in position all table mounted retractor blades hold reasonably still relative to the table but not necessarily the spine. This is because they do not fix to the patient and when the patient's spine moves e.g. during impaction or positioning of implants, or other vigorous work, the lateral retractors tend to bounce and slip. In that case, soft tissues including vessels can slip under or around the retractor blades.

Contact with the bone by providing an additional point of stability helps reduce this, but even with the Brau retractor, it remains a problem. If a constant force is applied from the frame along the line of the blade, pushing the blade against the spine, this helps stability, but has little resistance to the blade slipping or sliding posteriorly and causing tissue injury when the spine moves. It is preferable to minimize the amount of retraction used and to use smooth retraction over an area, particularly when retracting blood vessels in order to reduce turbulence and thereby the potential for thrombosis within the vessel.

It is known in current surgical practice to employ a bone anchor to secure a ligature such as may occur in tendon or ligament repair. The invention described herein is capable of engagement with soft tissue (non-bony) structures as well as bony structures. Although bone fixation is a well known and commonly used technique in establishing the retraction required, particularly in spinal surgery, there are some disadvantages occasioned by the hardware used and its fixation. For instance, screws have sharp ends which can cause injury to adjacent structures, particularly soft tissues structures should a screw slip on hard bone during insertion as significant force is applied. A further problem encountered in bone fixation is that weak bone can be damaged by the screw. Also retraction hardware can become dislodged by screw loosening or unwanted withdrawal where screws are held in weak bone.

By its rigid nature, bone fixation will result in setting a fixed retractor blade position. If it is incorrectly or inconveniently set in position the surgeon may be faced with a sub optimal, possibly obstructed surgical approach path to the surgical site which may not have occurred had an alternative screw position been selected. Generally, once the fixation has been selected and set, there is little or no capacity for adjustment of the retraction hardware to, for instance, improve the surgical approach path or to allow for improved angles. Furthermore any forces on retractor blades can lead to levering on bone anchors with resultant bone injury and anchor loosening.

It is desirable for a blade of a retractor blade assembly to have some capacity for adjustment once the assembly is anchored in position to allow for tool repositioning or to improve the approach path to the anatomical site to be corrected by the surgery. Repositioning of bone anchors once initially set potentially increases bone damage as the screws require bone openings for fixation. Drilling and redrilling these openings is most undesirable and the openings themselves may bleed. Repeated drilling to reset an anchor can risk loosening in the rest retraction assembly.

Background to Use of Tissue Fixation

In Anterior lumbar spinal fusion surgery there is a need for stability of retractors in order to protect and avoid injury to critical structures. Most commonly this surgery occurs at the spinal disc space. In typical spinal fusion surgery a region of this disc has to be exposed in order for a "window" in the disc to be created, through which the contents of the disc are removed prior to insertion of a cage inside the disc space through this window. Bone graft material may be placed in or around the cages inside the disc space in order that the bone may fuse i.e. grow across the disc space. Various spinal retractors are known that are used to expose these windows into the disc space. Typically the boundary regions around these windows include vital structure e.g. nerves or major blood vessels. Protection and avoiding injury to these structures is critical.

There are presently 4 broad categories of retractors that are widely used.
1. Those where blades are fixed to the bony spine using pins or screws.
2. Those that are attached via a fixation system to the sides of the operating table.
3. Those that are hand held by an assistant,
4. Blades that pivot or lever off the spine via a point on the end of the retractor.

This last group maybe externally held by a table mount or hand held by an assistant. Stability of such retractors is critical to maintain the working space safely as sharp or strong tools may be used close to delicate structures.

The following provides additional information on the above 4 groups:
1. The rigid fixation and stability of bone fixation is preferred by some, but the use of sharp screws into bone can be dangerous, if screws are initially misplaced or the bone screw interface fails resulting in loosening of the retractor or unwanted movement of pointed sharp screws. Such retractors are not easily adjusted.
2. Some surgeons prefer smooth ended table mounted retractors, these usually rest on the spine but primary stability comes from being held externally. Table mounted blades via complex arms or rings tend not to be completely stable, as the patient's spine may move relative to the table during surgery requiring large forces to be applied to the spine.
3. Assistant held retractors are the least stable system as assistants may not be able to see and are mechanically disadvantaged.
4. Pivoting or levering retractors have more stability than purely handheld retractors from their engagement between point of retractor and spine, but they are stable less than bone fixed blades. They also share the dangers as bone screws namely sharp points of the retractor blade may displace. They also still require an external fixation source be it an assistants hand, or a table mounted arm or ring. Thus there is a need for improvements in this area.

Prior Art Use of Hooks

Hooks may be used as retractors on handles, on elastics. These are used typically to retract skin, as the hook formation being very superficial can be easily disengaged. Retractors are known that have enlarged teeth, that are part of or protrude from a distal edge of blade in order to improve grip on tissues. Typically teeth engage muscle; E.g. McCulloch blades, Cloward blades. The aforesaid blades are known with different sizes and different shaped teeth-teeth that hook upwards, parallel or nearly parallel to their blade. True hooks are not known in routine use, as these would be difficult to engage and remove Although there are a wide variety of retractor blades currently in use, there remains room for improvement to achieve the desirable objectives described earlier; ease of insertion/anchorage, adjustability through multiple degrees of freedom to create an optimal surgical access path and efficient maintenance of retraction of soft tissue and avoidance of obstruction of the surgeons path to the operating site and finally stability that does not compromise retraction in the event of unwanted loading such as inadvertent bumping during surgery.

INVENTION

The present invention addresses the problems associated with the known retraction blade assemblies and seeks to improve the aforesaid existing retractor systems by providing a retractor blade assembly which includes a support member having a distal end formation which allows anchorage to soft tissue or bone and which is capable when anchored, of displacement and adjustment without having to redrill or re anchor the assembly anchorage. The invention provides improvements in the distal end geometry of the blade enabling increased versatility in the nature of the blade assembly engagement to anatomy and also allowing increased latitude for movement and adjustment of the blade and blade support member once anchored in position. This enables optimisation of soft tissue retraction and blade movement which efficiently distributes soft tissue loads applied on the blade and enables a surgeon to adjust path attitude to the surgical site. The present invention also contemplates anchorage by engagement with soft tissues and/or bony anatomy increasing the versatility in post setting adjustment to improve or change the attitude of tools used during surgery and to enable fine and substantial adjustment of the surgical approach path.

One embodiment of the present invention is particularly adaptable to soft tissue anchorage engagement and more particularly tissue anchorage during spinal surgery, which encounters the anterior longitudinal ligament having vertical running fibres and which is the strongest ligament in the body. This ligament crosses outside the disc space. The disc annulus i.e. the outside includes interlacing fibres and internally a jelly like nucleus. In spinal fusion surgery as much as possible of the disc nucleus and annulus is removed and replaced with cages and graft material. This is performed through a window in the disc annulus which may be on the front, side or back of the disc.

The present invention according to one embodiment, provides a retraction assembly which retracts soft tissue back away from the surgical site but which also allows hard or soft tissue engagement and a capacity to at least orthogonally or rotationally adjust a reactor blade to set an optimal surgical path to the surgical site. According to one embodiment a retractor blade is mounted to a support member which has a distal end formation which is connectible to soft tissue anatomy and allows adjustment of the attitude of the retractor blade while the distal end of the support member is connected to the soft tissue. The soft tissue anchorage may be provided by a ligament or annular fibres of disc immediately adjacent the spine. This enables separately or in combination, maintenance of the operative field by retraction of tissues which would otherwise obscure a surgeon's view and out of an optimal visual path to the surgical site, avoidance of injury to retracted soft tissue and a capacity for adjustment of blade position at least through but not limited to arcuate rotation.

According to one embodiment, there is provided a support member having a proximal end and distal end, the distal end including a formation which engages soft tissue or bone, a retractor blade which engages and is supported by the support member, the formation allowing the retractor blade when mounted on the support member to be adjusted through at least one degree of freedom to facilitate retraction of tissue and optimisation of a surgical path.

According to one embodiment the distal end of the support member includes hook or hook like formation that engages soft tissue such as a ligament or annulus. Preferably the hook or hook like formation is adjustable relative to the retractor blade when mounted on the support member. Preferably the hook and distal end of the retractor blade can be arranged such that the distal end of the blade engages spinal bone while the soft tissue is engaged by the distal formation. This setting geometry of the retraction assembly minimises the hardware inside the disc space while allowing a pivoting or rotational adjustment of the blade.

This retraction assembly according to the invention seeks to improve the stability of retractor blades during anterior lumbar surgery, irrespective of whether relying on bone or soft tissue anchorage. The invention provides an alternative blade assembly that improves the versatility of retraction blade setting compared to existing systems. Although designed to aid surgery on the anterior lumbar spine the principles have application throughout the spine and elsewhere where soft tissue and/or bone are available for anchorage.

In its broadest form the present invention comprises:
  a retraction assembly for use in retracting soft tissue during spine surgery; the assembly comprising; a reactor blade having a blade body and first and second ends, a support member comprising first and second ends, the second end of the support member including an anchorage capable of anchoring the assembly to an anatomical structure while allowing movement of the support member, the retractor blade capable of detachable attachment to the support member.

According to one embodiment the anchorage includes a formation to enable attachment of the anchorage to bone. According to an alternative embodiment the anchorage includes a formation to enable attachment to soft tissue. In the embodiment attachable to bone, the formation allows screw fixation to bone. In an embodiment attachable to soft tissue the formation comprises a hook or hook like structure which engages the soft tissue.

Movement of the support member involves free movement of the second (distal) end to enable adjustment from one position adopted during insertion of the assembly to at least one other alternate position relative to the first insertion position. This enables capability for wide adjustment of the retractor or blade to achieve an optimal retraction positions and geometry to best suit the surgeon's view of and approach to the surgical site. According to one embodiment the anchorage is integral with the support member. According to an alternative embodiment the anchorage is integral with the retractor blade. In one embodiment the support member is pivotally attached to the anchorage.

In another broad form the present invention comprises:
a surgical retractor blade assembly for retraction of soft tissue during spinal surgery, the assembly comprising at least one support member having a proximal end and a distal end; a retractor blade adapted to detachably engage the at least one support member, the distal end of each support member including a formation which enables anchorage of the distal end of the support member and freedom for the proximal end of the support member and attached blade to undergo displacement such as arcuate or rotational movement.

In another broad form the present invention comprises:
a retraction assembly for use in retracting soft tissue during spine surgery; the assembly comprising; a reactor blade having a blade body and first and second ends, a support member engagable with the blade body and comprising first and second ends, at least a part of the first end engaging a passage in the blade body and the second end of the support member including an anchorage capable of anchoring the assembly to an anatomical structure while allowing movement of the support member, the retractor blade capable of detachable engagement with and movement relative to the support member.

According to a preferred embodiment, the support member is rod like and locates in an elongated recess in the retractor blade. According to one embodiment, the anchorage is a hook formation which is capable of engaging soft tissue. According to an alternative embodiment the anchorage is capable of direct or indirect fixation to bone.

In another broad form the present invention comprises:
a retraction assembly for use in retracting soft tissue during spine surgery; the assembly comprising; a reactor blade having a blade body and distal and proximal ends, a support member engagable with the blade body via an elongated recess along the blade and having proximal and distal ends; at least a part of the proximal end engaging a passage in the blade body and the distal end of the support member including a connection which engages an anchorage capable of anchoring the assembly to an anatomical structure while allowing movement of the support member and retractor blade, the retractor blade capable of detachable engagement with and movement relative to the support member, the proximal end of the support member including means to retain a locking nut to lock and adjust the support member.

The present invention provides an alternative to the known prior art and the shortcomings identified. The foregoing and other objects and advantages will appear from the description to follow. In the description reference is made to the accompanying representations, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying illustrations, like reference characters designate the same or similar parts throughout the several views. The following detailed description is, therefore, not to be taken in a limiting sense, and the scope of the present invention is best defined by the appended claims. It will be convenient to hereinafter describe the invention in relation to metallic materials in the present exemplary applications. However, it is to be appreciated that the assemblies described herein may be constructed from other materials such as plastics.

BRIEF DESCRIPTION OF THE DRAWINGS

The present invention will now be described in more detail according to a preferred embodiment but non limiting embodiment and with reference to the accompanying illustrations, wherein:

FIG. 34a-f shows a support member according to various views and having alternative geometry and a flexible distal hinge.

DETAILED DESCRIPTION

Figure 1:
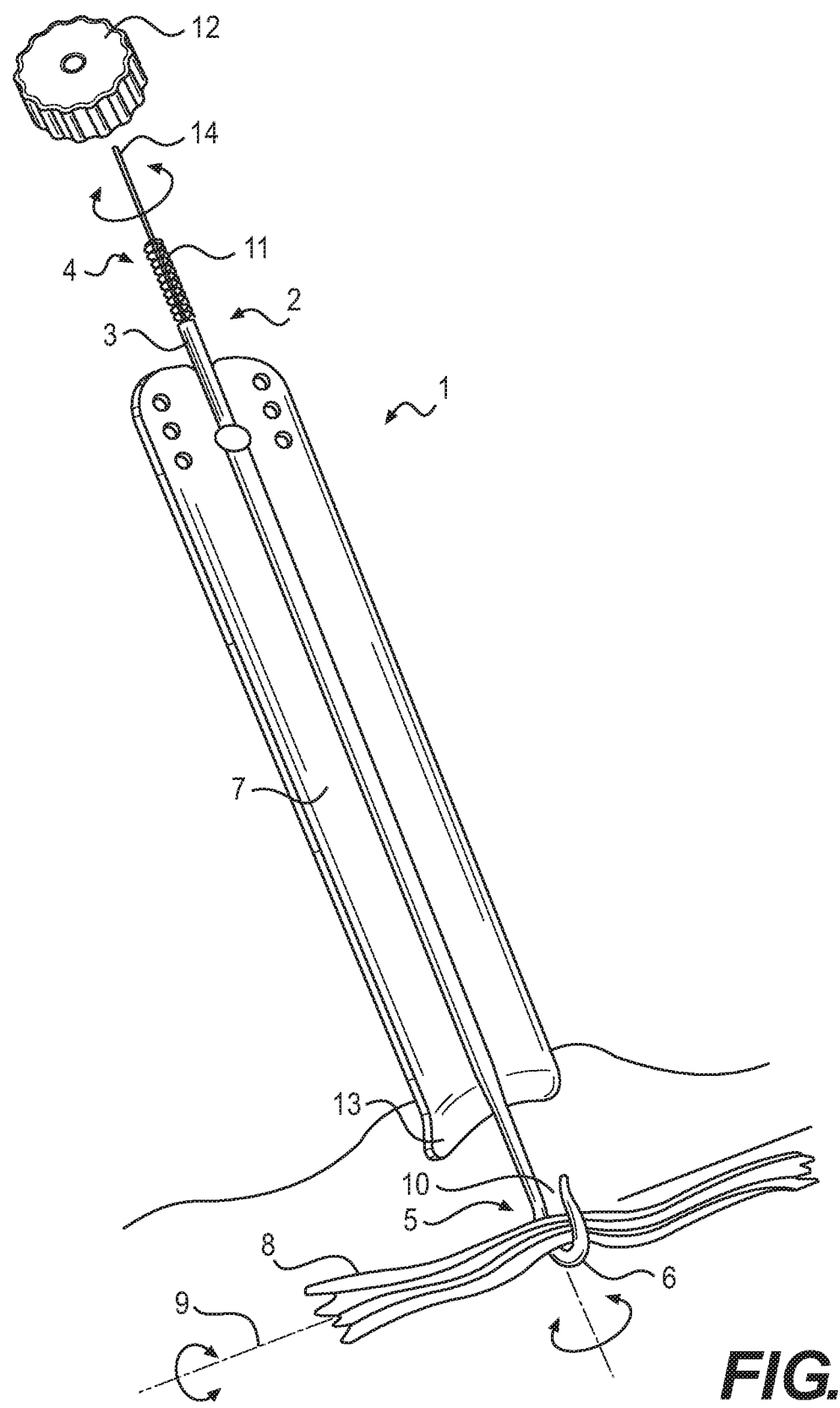
FIG. 1 shows an exploded view of a retractor assembly employing a support member with hook formation according to one embodiment.

Referring to FIG. 1 there is shown, a retraction assembly 1 according to one embodiment. Retraction assembly 1 includes a support member 2 comprising a body 3 having a proximal end 4 and a distal working end 5. Distal end 5 is a free end and terminates in a hook (or hook like) formation 6. Body 3 of support member 2 is capable of engagement with a retractor blade 7 which co-operates with body 3 of support member 2. Throughout the specification a reference to a hook can be taken to mean a return where an end of a member turns back on itself at least to a limited extent so that the end of the member is after a return, pointing in a direction anywhere between 1-180 degrees from a longitudinal axis through the member. This includes L or U shapes and oblique angles. Support member 2 may be used independent of retractor blade 7 or in conjunction with blade 7. Hook formation 6 allows engagement with soft tissue 8 such as a ligament of a patient and once engaged body 3 can be moved and adjusted rotationally relative to a notional horizontal axis 9 through hook formation 6 and relative to a vertical axis 14 through body 3 of support member 2. Traditionally retractors are supported from a proximal end and usually engage (retract) soft tissue anatomy and anchor in vertebral bone.

Touch engagement with bone has been adopted to resist unwanted movements of the retractor blade responsive to a retraction force at a distal end. The blade traditionally retracts soft tissue behind it while restrained at the proximal end with a holding tool or suitable apparatus. According to the embodiment described, the hook formation 6 loops around soft tissue 8 to provide restraint at the distal end. Hook formation 6 is essentially a return portion which defines a recess 10 which allows receipt of soft tissue therein. In use, support member 2 engages retractor blade 7 via body 3. Proximal end 4 of support member 2 terminates in a threaded region 11 which receives and retains locking nut 12 to secure blade 7 to support member 2. Blade 7 may be adjusted longitudinally along support member 2 depending upon the relationship required at the distal end between the distal end 13 of blade 7 and the engagement between soft tissue 8 and hook 6.

Figure 2:
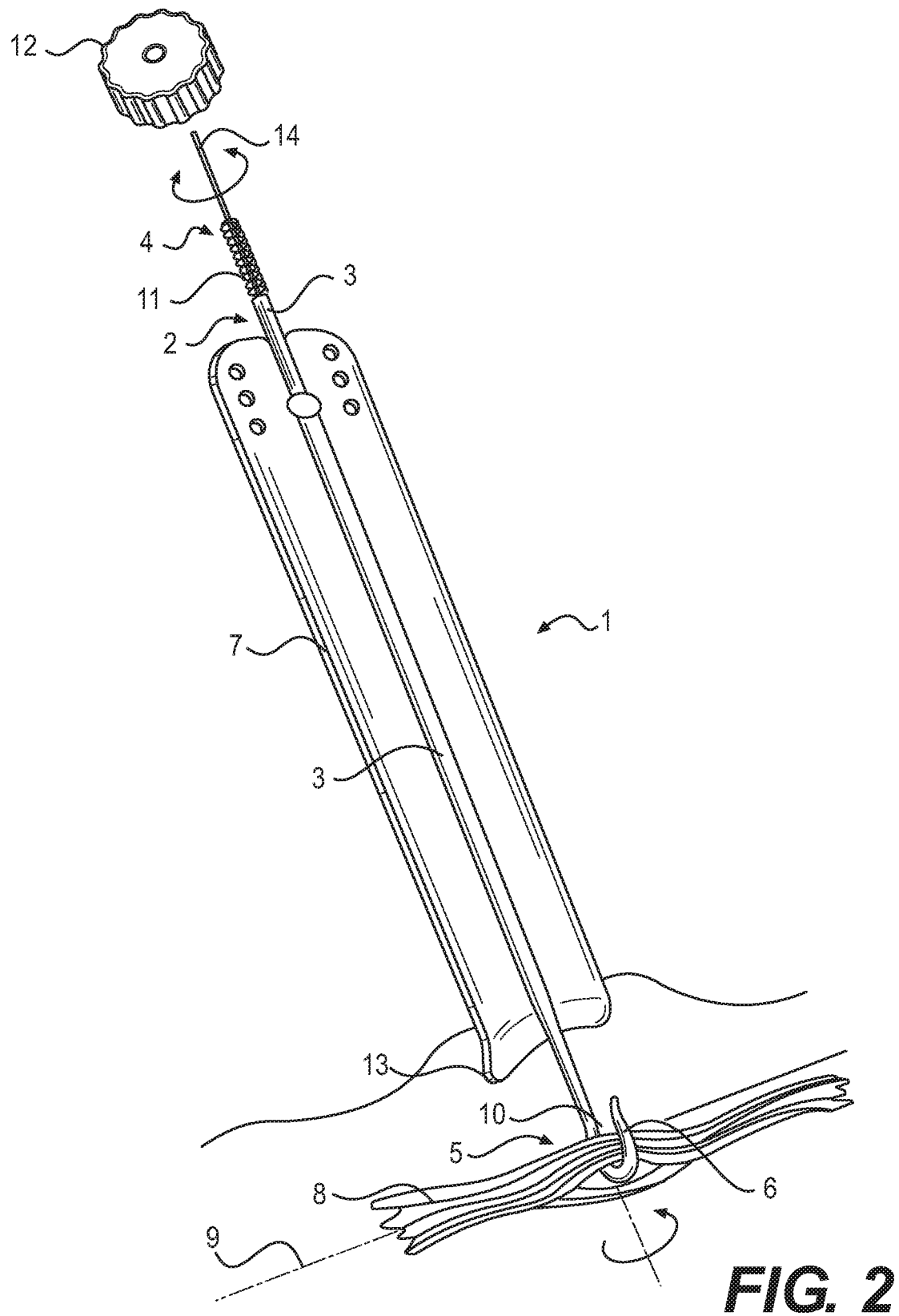
FIG. 2 shows a perspective view of the support member of FIG. 1

FIG. 2 shows with corresponding numbering a perspective view of the retraction assembly 1 of FIG. 1 showing the hook formation 6 engaging through an incision in a soft tissue ligament 8.

Figure 3A:
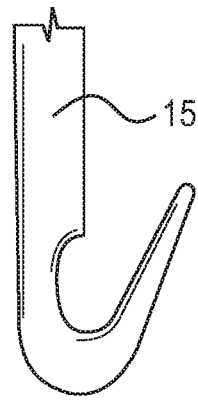
FIG. 3a and FIG. 3b show a possible alternative hook like formations employed on a distal end of the support member.
Figure 3B:
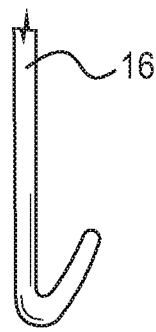
Figure 4A:
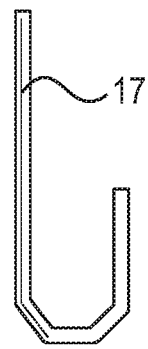
FIG. 4a and FIG. 4b show an enlarged hook according to one embodiment and engaging soft tissue.

FIGS. 3a & b show alternative geometry of hook like formations 15, 16 employed on a distal end of a support member. FIGS. 4a & b show possible alternative hook like formations 17, 18 employed on a distal end of a support member. It will be appreciated by persons skilled in the art that a variety of hook or hook like formations are feasible for engagement with soft tissues to provide an anchorage to enable adjustment of an attitude of blade 7. Various materials of construction are contemplated including metals and plastics including rigid and elastic plastics and a variety of distal end geometries for the support member 3 are also contemplated. Typically, a support member would preferably fall within the range of 1.5 mm-3 mm across (width or diameter) and may extend from 50-200 mm in length to suit length of the blade. A typical length of support member 3 is in the range of 100-150 mm. Preferably, a leading end of the hook formation 6 is thinner than the body of the support member to facilitate more convenient push though the soft tissues. Preferably, the distal end tip is pointed or rounded to penetrated the ligament. Preferably, the hook is less than 6 mm in width. Typically a hook formation might according to one embodiment resemble the geometry of a crochet needle and is thin enough to be passed along a passage along the retractor blade to effect the desired co-operating engagement.

The various hooks shown (6, 15, 16, 17 and 18) and contemplated co-operate with a blade 7 to anchor the assembly and set the blade 7 at a selected attitude. The soft tissues suitable for interaction with the assembly described above include ligaments, annular fibres of a disc immediately adjacent the spine so as to maintain outside the operative field other tissues which might otherwise be susceptible to injury. The assembly is especially, though not exclusively, applicable for anterior, anterolateral and lateral spinal surgery on the disc space.

Figure 4B:
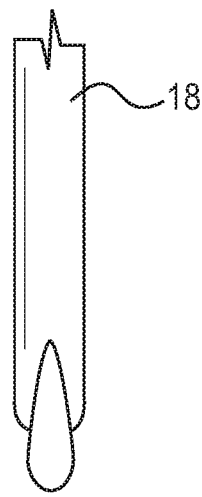

Preferably, the hook formation 6 is integrally attached to the support member 3. Alternatively the hook is detachable. In a further embodiment the hook is fixed to a support rod but the hook could be on a wire or thread and pushed through a ligament while held by another instrument. The retractor blade 7 and support member 21 may be connected in a manner other than that described including a key in slot or sleeve connection or a clamp. Leading edge of hook 6 maybe sharp as shown by items 15a and 18b in FIGS. 3a and 4b respectively to allow it to push through ligament parallel to the ALL fibres into the disc space avoiding the need to cut the ligament with a knife The support member and hence the hook formations may be adjusted relative to each other or adjusted in unison. According to one embodiment a hook formation is detachable from the support member to allow a selection of hook formations in the event that one selected is found unsuitable for the particular operative field. The distal end 13 of the blade 7 engages the spine at the same time as the hook engages soft tissues. The hook can be moved proximally to reduce the hardware protruding into the disc space. The hook and distal end of the blade co-operate and can allow relative adjustment including rotation and axial movements. The retractor blade is held in an optimal position protecting the disc window while the hook engages soft tissue (such as strong ligaments around the disc space or the edge of the annulus that forms the frame of the disc window, as an alternative to bone anchorage. The co-operation between the blade engagement and soft tissue anchorage via the hook formations render the retraction assembly stable and maintain their desired position around the disc window and on the spine. This addresses the natural and unwanted tendency of retractors to lift out of a wound assuming the path of least resistance. Hand held retractors slip unless a constant force is applied to them. Pivoting retractors loosen and table mounted retractors require strong mechanism to maintain this downward. Bone fixation avoids this but that has the disadvantages described earlier. One advantage of the present invention is in minimally invasive fusions of the spine These operations may use small skin incisions but have deep wounds. Long tools are required to be used at different angles to clean and prepare the disc space. If the retractor can move a little but still maintain the safe window without losing fixation, this is highly advantageous. Bone fixation typically prevents this or if the retractors are forcibly moved, screw loosening will occur. However, the connection to the ligaments in the examples described will allow some motion similar to pivoting but without the retractor losing fixation. Another advantage of such a system is where bone is very weak e.g. osteoporosis and screws do not hold well. The natural strength of the annulus and ligament may provide better retractor fixation than bone in these circumstances.

In use, a knife cut is made in the ALL and/or disc annulus parallel to the ligament fibres and a tapered hook is passed through the All and annulus of the disc into the deeper annulus or nucleus. The hook is then rotated 90 degrees away from the line of the fibres about vertical axis 14 (see FIG. 1) and withdrawn with the sharp point penetrating the ALL from within and to engage ligamentous tissue and resist further withdrawal. Since ligamentous connections to bone are very strong, this provides a good anchorage for the retraction assembly. Tightening nut 12 brings the hook 6 and blade 7 towards each other and if the hook has been rotated to predetermined position, the elbow of the hook may compress soft tissue against the base of the blade clamping the tissue and increasing the fixation to the soft tissue.

Attachment to soft tissue allows limited amount of movement unlike fixed bone screw and anchor. This is advantageous as it allows movement of a wound without complete loss of fixation. Withdrawal of hook 6 and engagement with the Anterior longitudinal ligament 8 (ALL) and annulus ensures a limited amount of the hook 6 inside a disc which would impede disc removal tools. Referring to FIG. 1, locking nut 12 urges blade 7 against a spine and secures the assembly. Blade 7 may be passed over body 3 and coupled axially or laterally. When removal is required, locking nut 12 is loosened and the blade removed. The hook formation 6 is then urged forward and rotated to be freed from the ligament 8. Ligament 8 could also be cut to release the hook. Another method to remove the hook is to overtighten the nut and rear hook through the ligament. During the removal, blade 7 may be left in position to protect other soft tissue during removal of the hook.

The combination of a support member terminating in a hook formation which engages soft tissue, releasably engages a retractor blade, allows mutual adjustability and functionally co-operates with it during use, is not known in the relevant filed of prior art.

There are many advantages imparted by the assembly described herein including but not limited to:

1. Securing blade 7 close to hook 6 i.e. at desired position.

2. Limits blade and hook motion by tightening relative motion.
3. Provides retractor stability but unlike typical bone fixation allows some motion e.g. axial rotation, flexion, extension, lateral bending but limits pull out and prevents posterior structures creeping under blade
4. Soft Tissues themselves may be used to provide grip for retractors, as distinct from retraction by flat surface of a retractor blade.
5. Overcomes the disadvantage of tearing and stretching muscle with commonly used sharp toothed retractors.
6. The assembly enables the use of previously unused strong Ligaments around spine and disc annulus Although a hook formation is a preferred embodiment on the distal end of the support member 3, other formations at the distal end of the support member are contemplated for engaging soft tissue, such as a forceps arrangement, clip compression plate to compress soft tissue, Kerrison forceps, toggle or expanding bolts, clips having jaws to engage the soft tissue, snap shut clips, staples, sutures or conventional tissue anchor.

A variable length hook or a hook which allows variation of the distance between the hook root and the distal end of the retractor blade is preferred. In use, it is important for the distal edge of the blade to be kept firmly against the spine to prevent unwanted prolapse of soft tissue under the distal edge into the surgical field. The length of the tissue engaging formation for engaging soft tissue is an important parameter. With a fixed length hook that is too long, the hook may over penetrate the disc space and if the blade is kept pushed against spine (for stability and to prevent tissue creeping beneath blade, the hook might then interfere with disc removal. Alternatively if a long hook is placed into disc space and then is pull backed to minimize the amount of hook inside the disc space, there would be a space left between the distal edge of blade and the spine allowing tissue to creep under blade around hook and into working field. A hook may not be long enough to penetrate the disc if the bone edges around the disc are elevated by osteophytes. A fixed length hook does not allow rotation of the hook to a preferred orientation. An ideal angle for penetration is with a leading edge of a hook parallel to the line of fibres, but an ideal angle to prevent pull out is with hook orthogonal to line of fibres. Ideally, a surgeon can exchange hooks (or blades) using the assembly of the present invention. In some cases a barbed hook (in the nature of a fish hook) might be selected. A secondary reverse point prevents withdrawal. This version would be useful when a blade passes across and down the side of the disc space e.g. in lateral alif. One other feature contemplated for the hook is a square formation on the top of the hook supporting member that can be rotated using matching wing containing square female portion. This is to rotate the hook when under the ligament.

Figure 5:
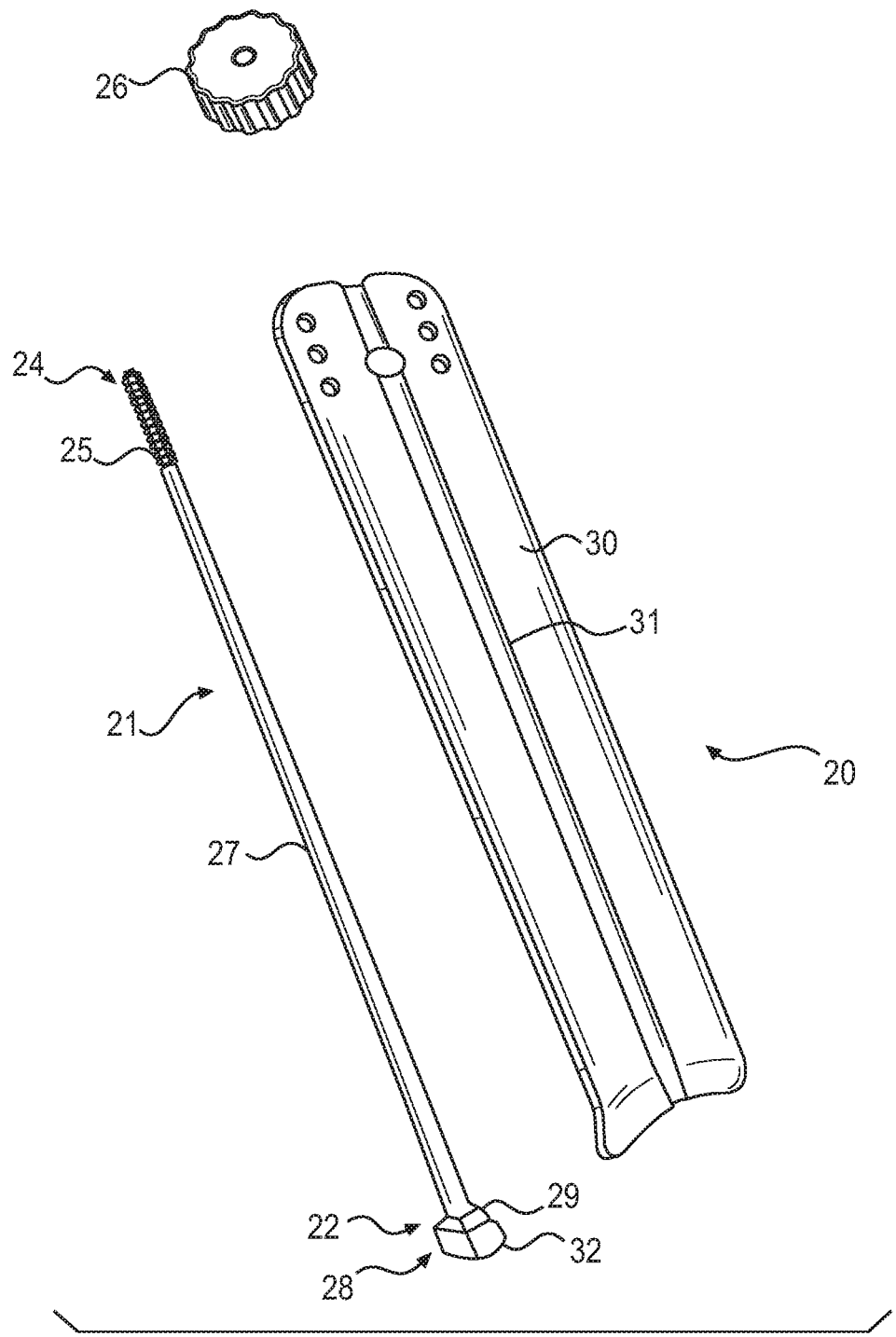
FIG. 5 shows an exploded view of a retraction assembly according to an alternative embodiment with a hinged formation at a distal end of the support member.

FIG. 5 shows an exploded view of a retraction assembly 20 according to an alternative embodiment. Assembly 20 comprises a support member 21 having a distal end 22 and proximal end 24. Proximal end 24 includes a threaded region 25 which when in use, receives and retains thereon a locking nut 26. Distal end 22 includes a hinged formation 28 which allows body 27 of support member 21 to rotate relative to and about hinge 29. Assembly 20 further comprises a retractor blade 30 which includes a longitudinal recess 31 to accommodate body 27 of support member 21. Hinged formation 28 includes an opening 32 which accommodates a pedicle screw (not shown) for fixation of hinged formation 28 to bone. When blade 30 is engaged with body 27 locking nut 26 secures blade from separation from support member 21. Hinged formation 28 allows blade 30 and body 27 of support member 21 to rotate in unison allowing adjustment of the attitude of the retractor during surgery. The blade 30 can be loosened or released by unscrewing locking nut 26.

Figure 6:
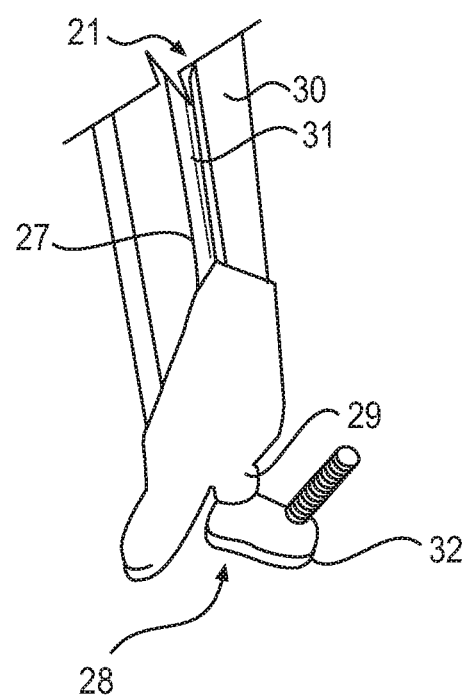
FIG. 6 shows an enlarged view of the distal end hinged anchorage formation of FIG. 5.

FIG. 6 shows with corresponding numbering an enlarged view of the distal end hinged anchorage formation 28 of FIG. 5 as it is attached to a bone anchor.

Figure 7:
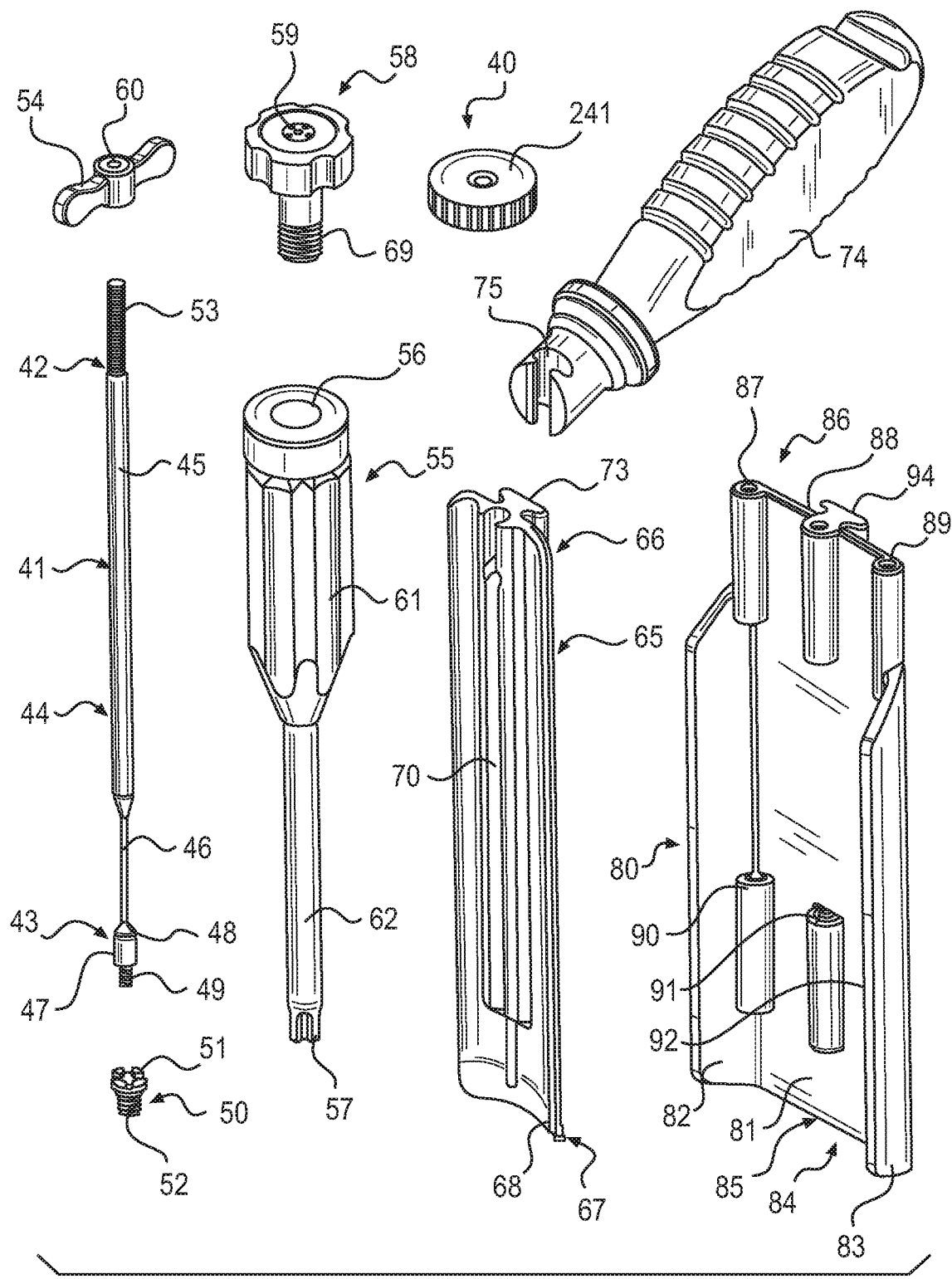
FIG. 7 shows an exploded perspective view of a third embodiment of a retractor assembly which engages a screw and allowing post insertion support member adjustment.

FIG. 7 shows an exploded perspective view of a third embodiment of a retractor assembly 40 which engages a pedicle screw for anchorage and allows post insertion support member adjustment. Assembly 40 includes a support member 41 having a proximal end 42 and distal end 43 and therebetween a body 44. Body 44 as shown has a wide region 45 and a narrow region 46. Narrow region 46 terminates in formation 47 which comprises a flared portion 48 and threaded shaft 49. Narrow region 46 has in built bending flexibility to allow movement of wide region 45 when adjustment is required. In use, threaded shaft 49 engages pedicle screw 50 via threaded recess 51 and pedicle screw 50 engages bone via threaded shaft 52. At proximal end 42 is a threaded region 53 which receives and retains wing nut 54. Support member 41 is inserted using insertion tool 55 which has a longitudinal hollow interior passage 56. Insertion tool has a distal working end 57 which is arranged to engage corresponding formations on screw 50 to enable insertion thereof.

Support member 41 is insertable into passage 56. This enables the insertion tool 55 to insert screw 50 and align support member to threaded recess 51 of screw 50. Insertion tool 55 is manually operated by turning handle 61 which operates working end formation 57 via shaft 62. Locking bolt 58 engages passage 56 via threaded region 57 and also includes a through passage 59 which receives proximal end 42 of support member 41. Wing nut 54 includes a through passage 60 which engages end 42 of support member 41 via a corresponding hex formation 63 (see FIG. 9). Once support member 41 is engaged with pedicle screw 50 and screw 50 is inserted into bone, retractor blade 65 is ready for engagement with support member 41. Retractor blade 65 has as proximal end 66 and distal end 67. End 67 has a contour 68 arranged to conform to bone contours. Disposed longitudinally along blade 65 is a through passage 70 which is arranged to accommodate body 44 of support member 41.

Once inserted inside passage 70, due to anchorage with screw 50, support member 41 and blade 65 can move in unison as a result of the flexibility of narrowed region 46. Nut 54 locks support member 41 to blade 65. Blade 65 also includes a longitudinal profiled part 73 along its back surface to receive and retain handle 74 via co-operating and similarly formed recess 75. Handle 74 is free to slide along formation 73 as required by the environment in which it is operating. Handle 65 may be used to induce the extent of bending required at region 46.

Also shown in FIG. 7 is an alternative retractor blade 80 which is physically larger than blade 65 and has an alternate shape. Blade 80 comprises a back wall 81, side walls 82 and 83. At distal end 84 is provided a contour 85 which accommodate bone contour when in use. At proximal end 86 are three openings 87, 88 and 89 which respectively along with openings 90, 91 and 92 (obscured behind wall 83) to receive one or more support members such as (but not limited to support member 41. This provides a much stronger retraction force and a stiffer flexibility for higher tissue pressures loads. Despite the increased stiffness when using multiple support members, the blade 80 is still adjustable to suit. Located on the back of wall 81 is a formation 94 which is profiled to accommodate recess 75 of handle 74. Handle 74 can slide along formation 94 in a similar manner to that described for retractor blade 65.

Figure 8:
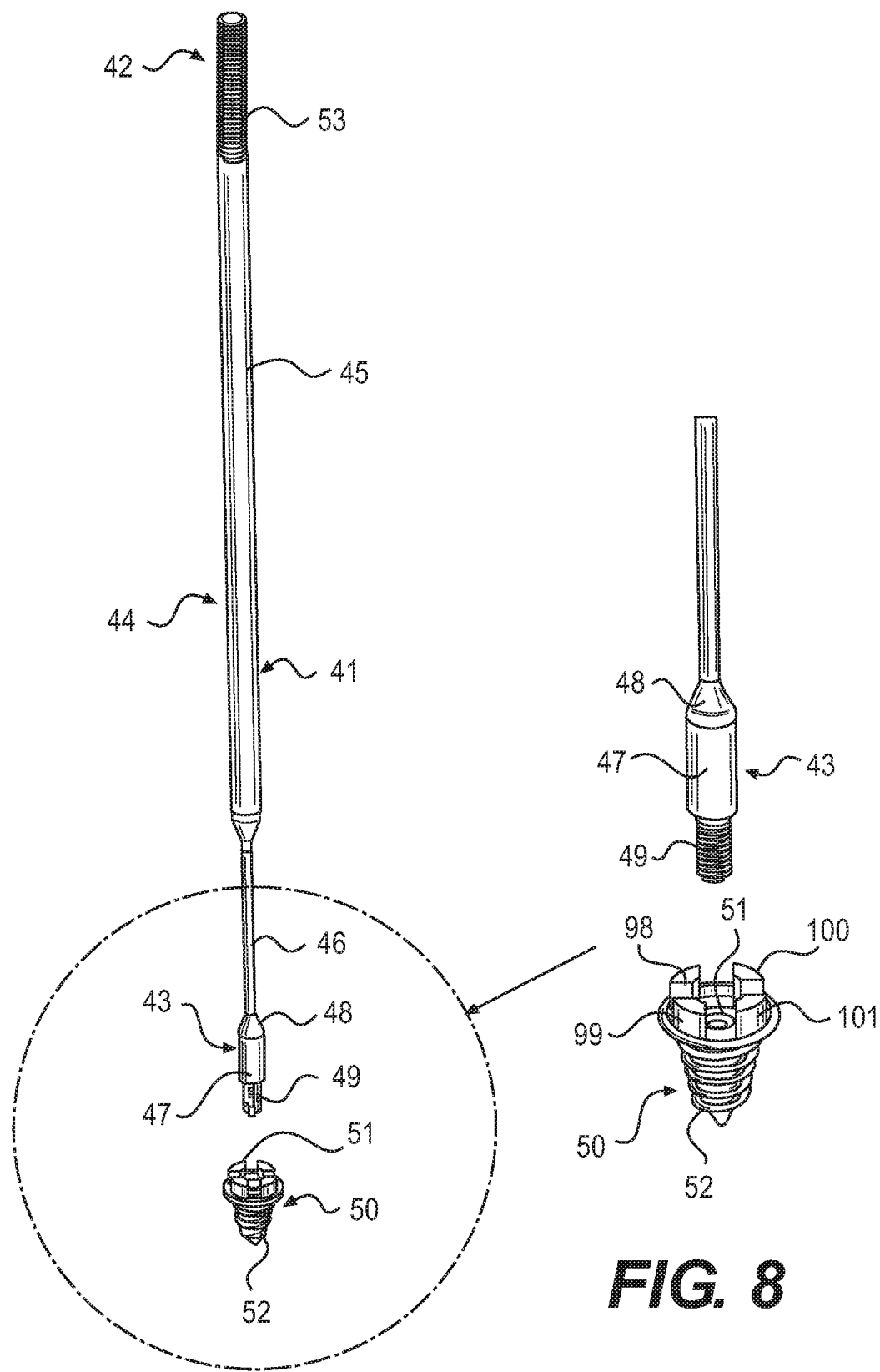
FIG. 8 shows an enlarged view of the distal end formation of the support member.
Figure 9:
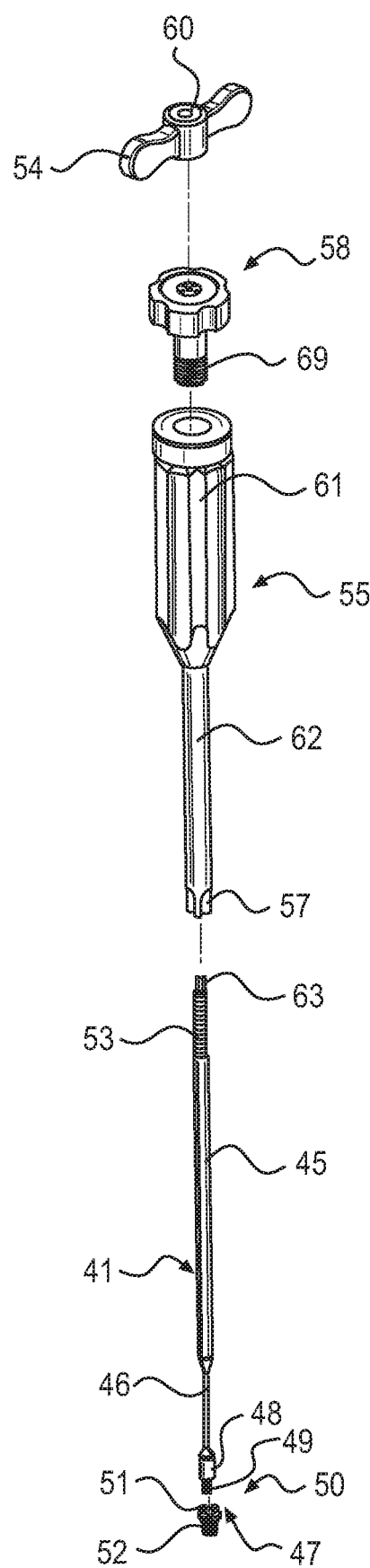
FIG. 9 shows an exploded view of the interaction between the insertion tool and the support member.

FIG. 8 shows with corresponding numbering, an enlarged view of the distal end formation 43 of the support member 41. With screw 50 enlarged the proximal end profile parts 98, 99, 100 and 101 which provide abutment surfaces for distal end formation 57 of shaft 62 of insertion tool 55 can be better seen. Threaded male end 49 engages threaded females recess 51 of screw 50. FIG. 9 shows an exploded view of the axial orientation and interaction between the insertion tool 55 and the support member 41.

Figure 10:
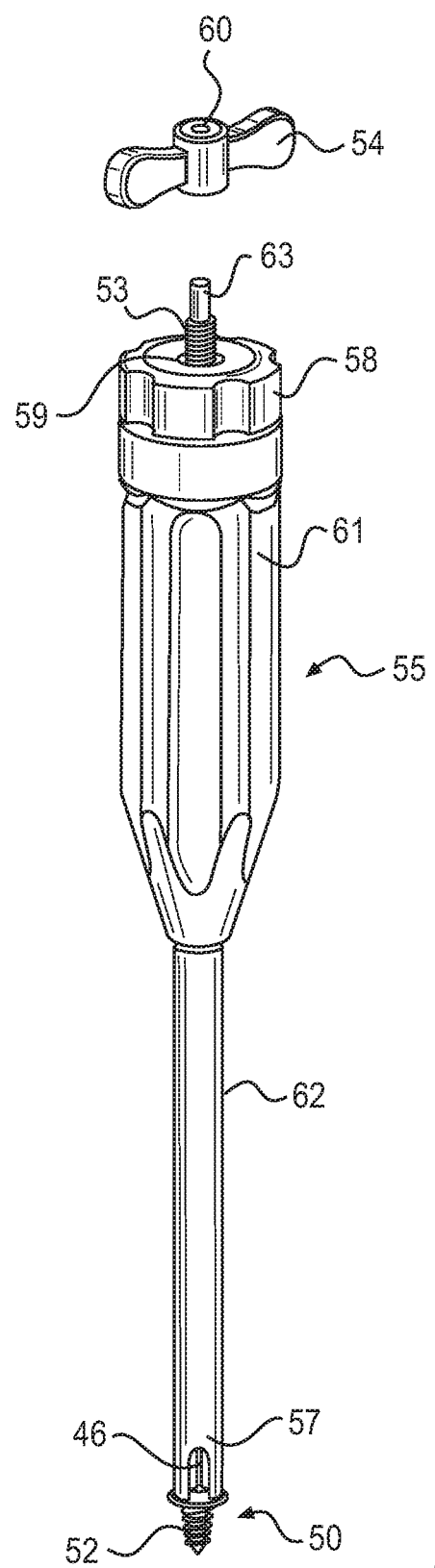
FIG. 10 shows the insertion tool engaged with the support member and pedicle screw.
Figure 11:
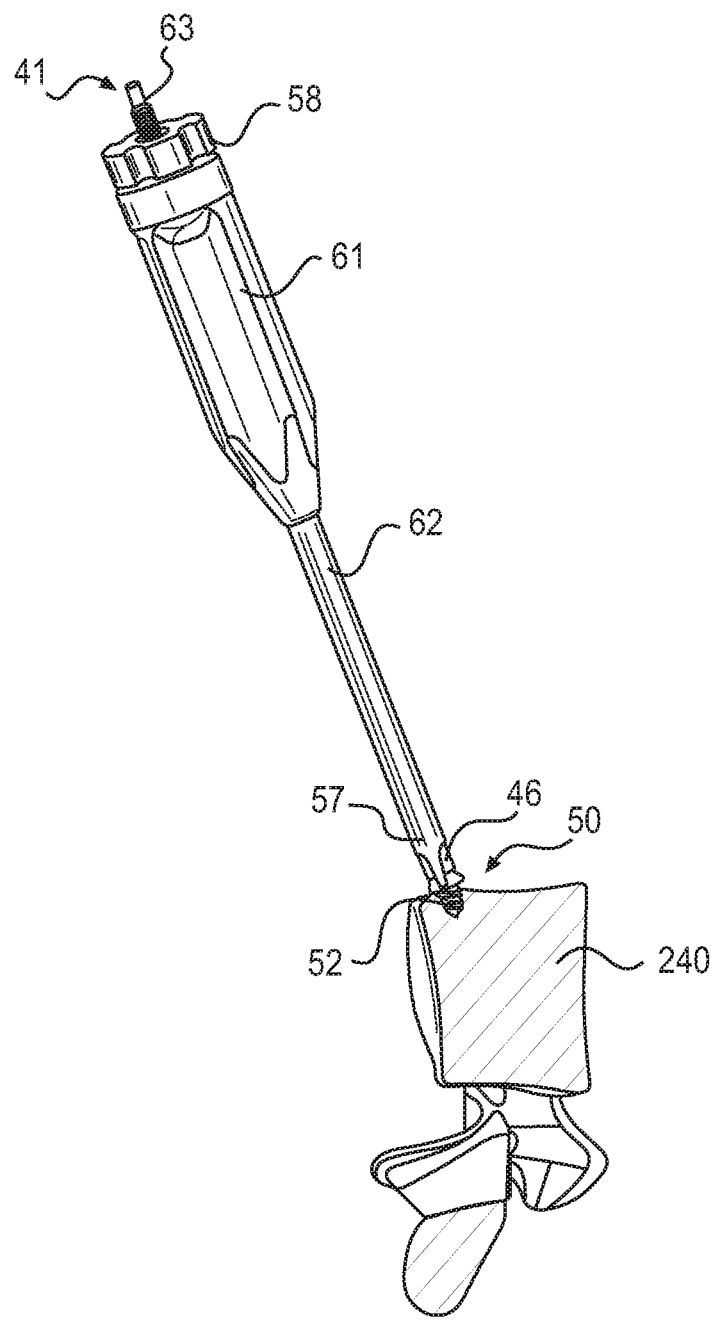
FIG. 11 shows a cross sectional view of vertebral bone with the support member retained in the tool for insertion.

FIG. 10 shows with corresponding numbering, the insertion tool 55 engaged with the support member 41 and pedicle screw 50 and prior to locking by locking nut 60. FIG. 11 shows a cross sectional view of vertebral bone 240 with the support member 41 retained in the tool 55 for insertion during insertion of screw anchor 50.

Figure 12:
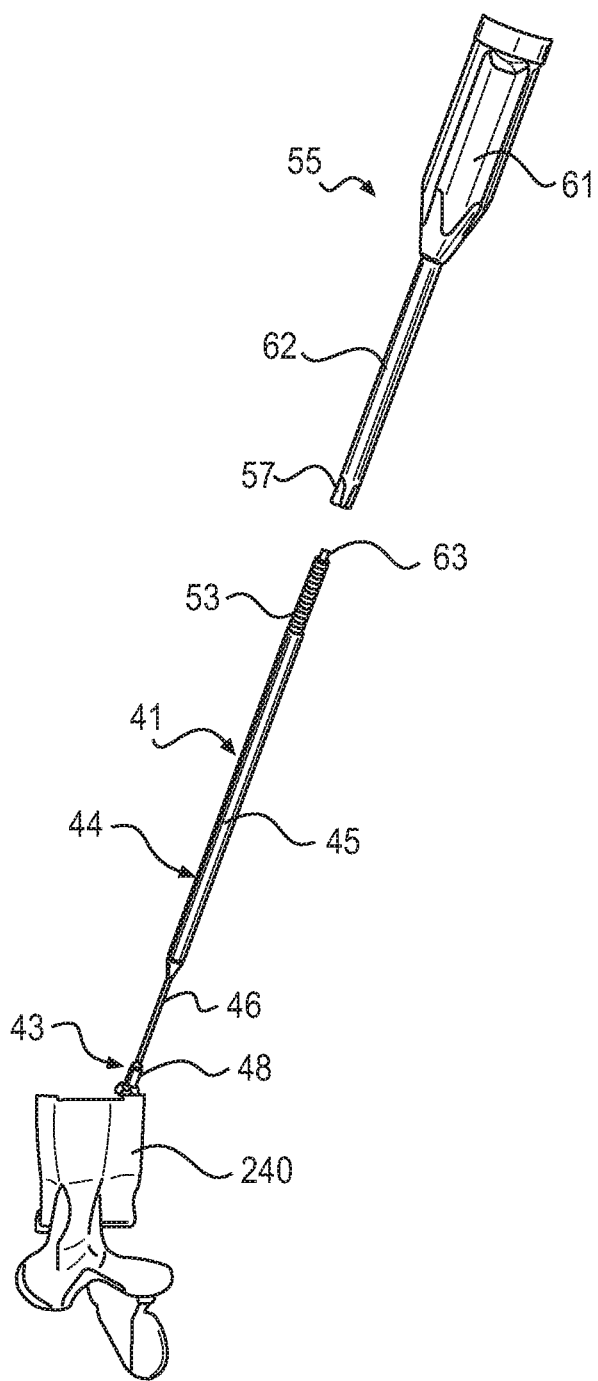
FIG. 12 shows the support member engaged to the pedicle screw and the insertion tool withdrawn after insertion of the support member.
Figure 13:
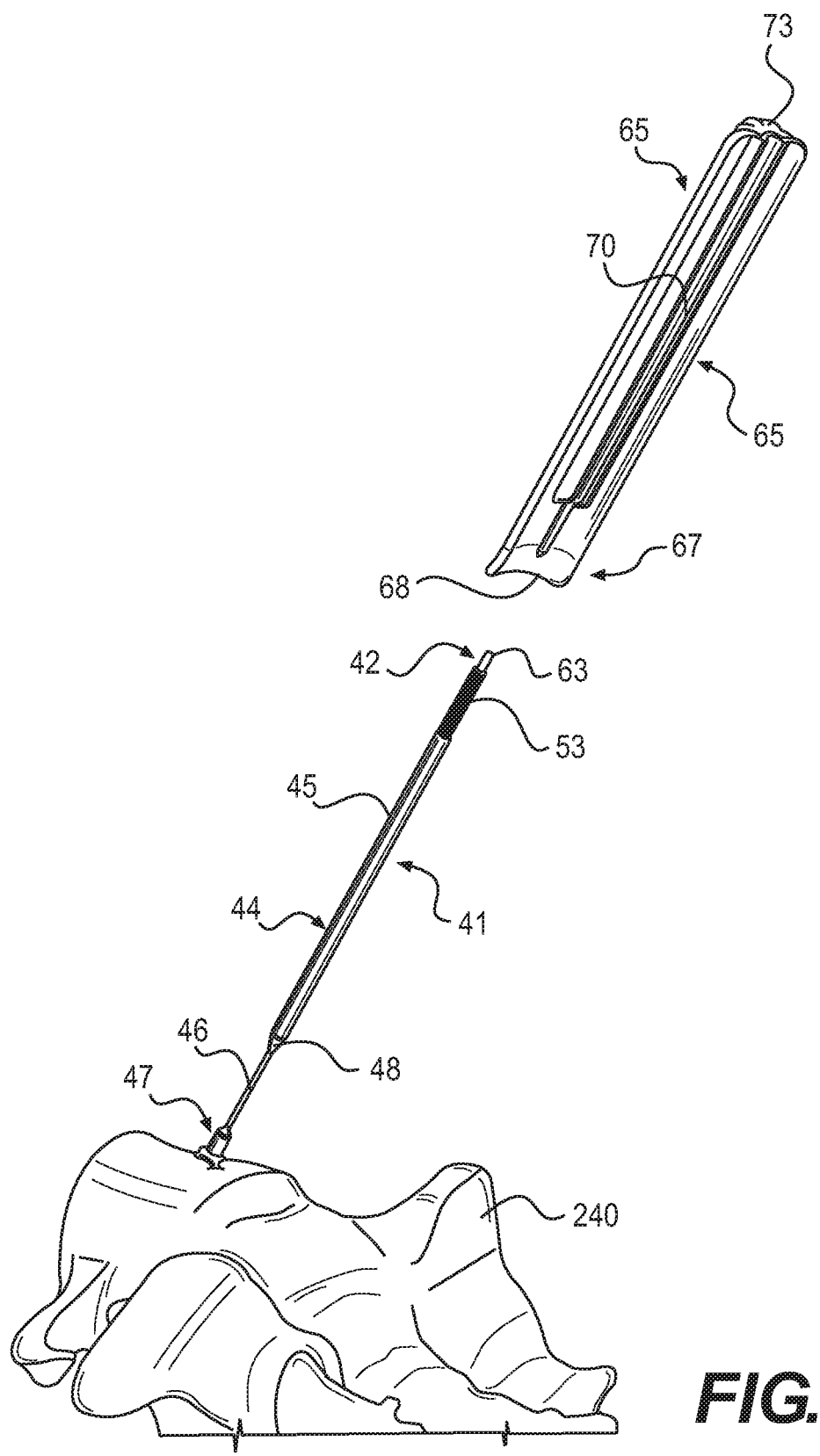
FIG. 13 shows the retractor blade prior to engagement with the support member.
Figure 14:
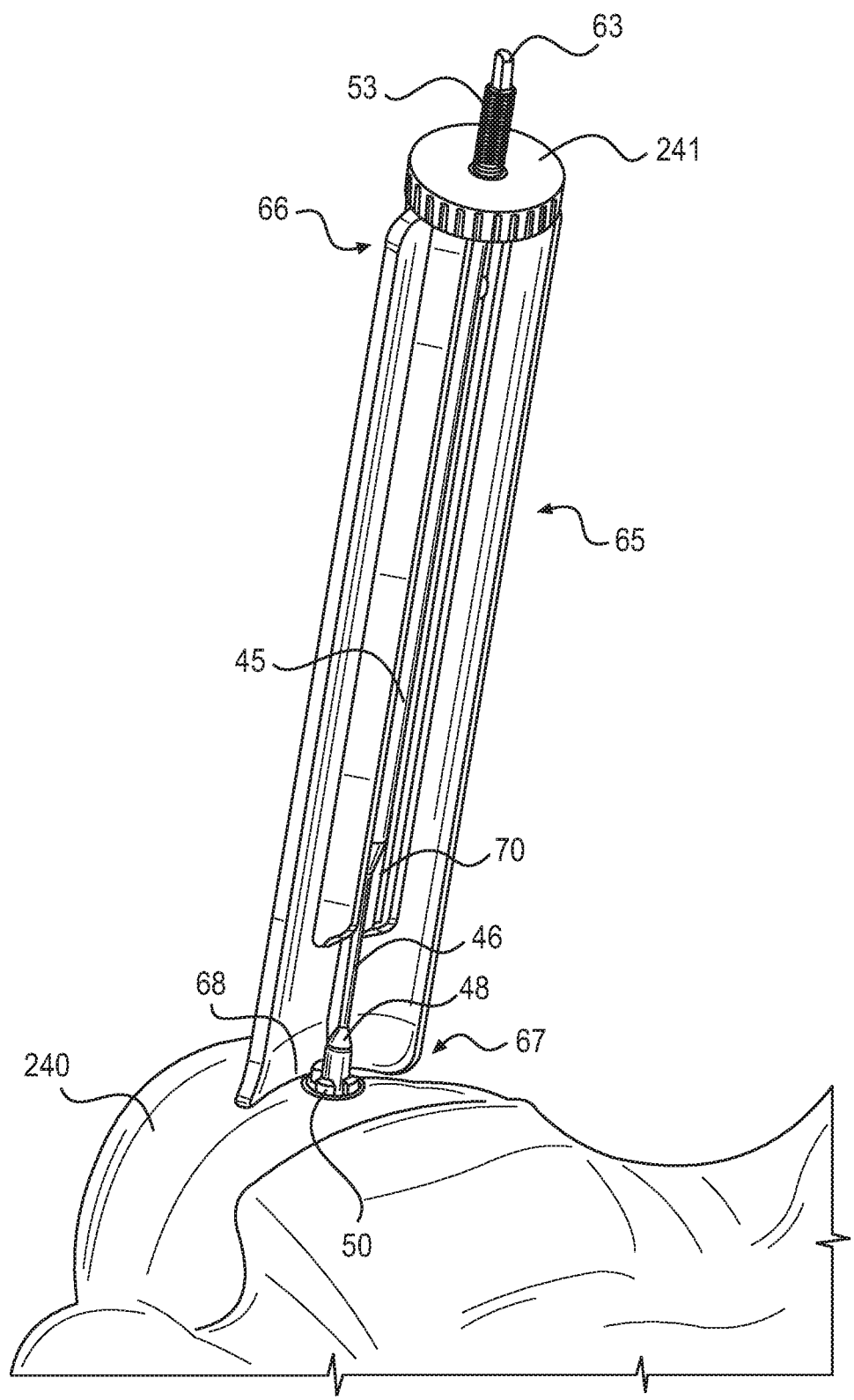
FIG. 14 shows the retractor blade engaged with the support member in a first orientation.

FIG. 12 shows the support member 41 engaged to the pedicle screw 50 and the insertion tool 55 axially withdrawn after insertion of the support member 41. FIG. 13 shows with corresponding numbering the support member 41 in position in vertebra 240 retractor blade 65 prior to engagement with the support member 41. FIG. 14 shows the retractor blade 65 engaged with the support member 41 disposed in a first orientation This is useful when a surgeon requires adjustment to the surgical approach path. Blade 65 is locked into position via nut 101. This integrates blade 65 with support member 41 and due to the flexibility of region 46 of support member 41, this allows blade 65 to on one hand be supported by support member 41 and on the other hand to be repositioned at different angles relative to a vertical axis through screw 50. The distal blade is shown with posterior curve but may be straight as this allows tissue compression when the hook is orientated backwards and withdrawn.

Figure 15:
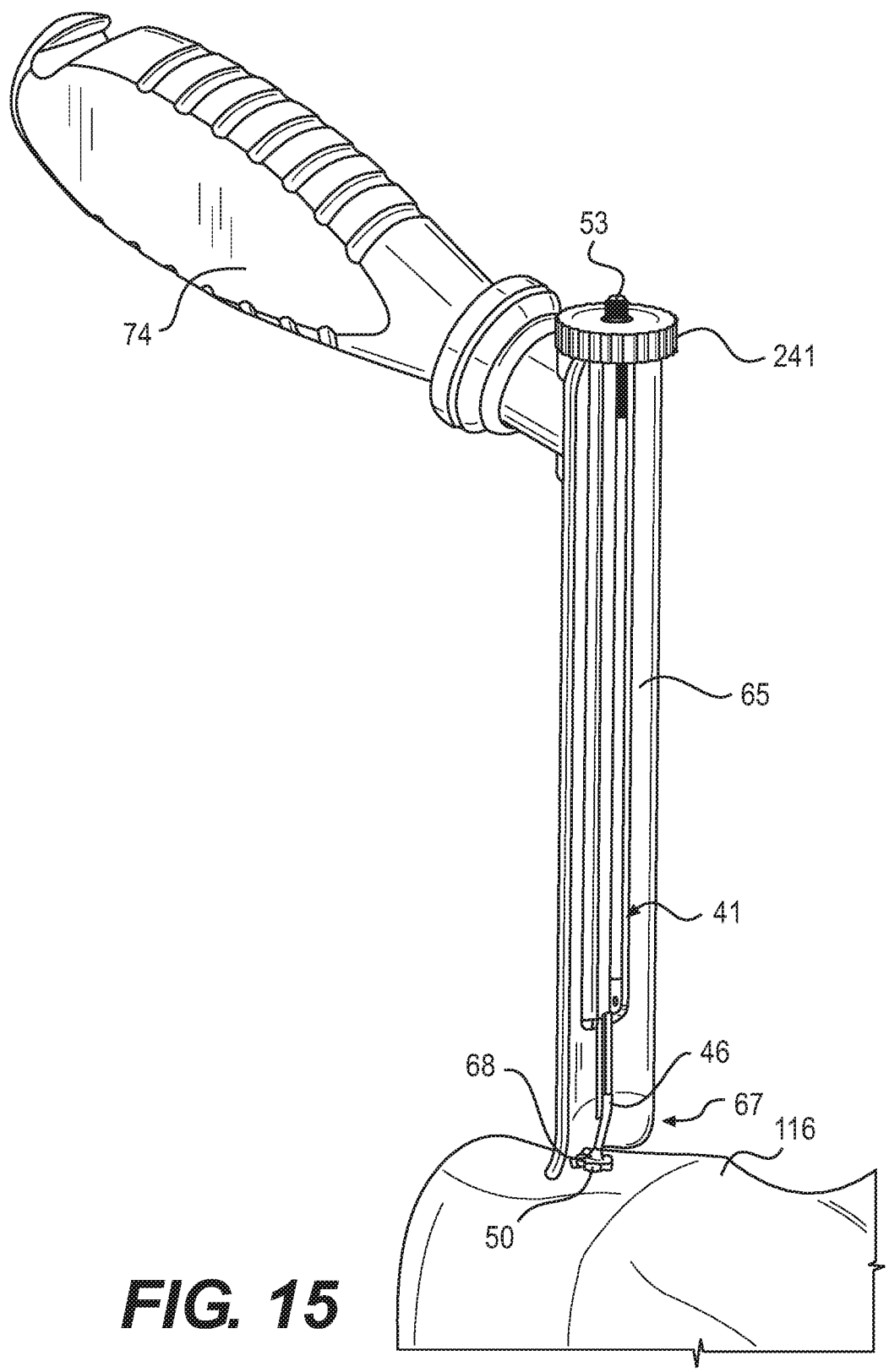
FIG. 15 shows with corresponding numbering the assembly of FIG. 14 in an alternative orientation.

FIG. 15 with corresponding numbering, the assembly of FIG. 14 in an alternative orientation. In this view handle 74 has engaged profile 73 (obscured) of blade 65. This facilitates rotation away from the orientation shown in FIG. 14 by flexure of region 46 of support member 41. Region 46 is no longer straight and has undergone bending which enables blade 65 to be disposed at a more oblique angle, relative to a longitudinal axis through the pedicle screw 50 located in vertebrae 116.

Figure 16A:
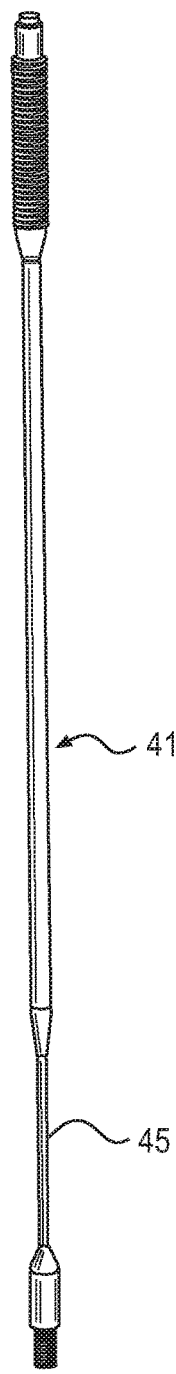
FIG. 16a,b,c shows alternative configurations for the support member.
Figure 16B:
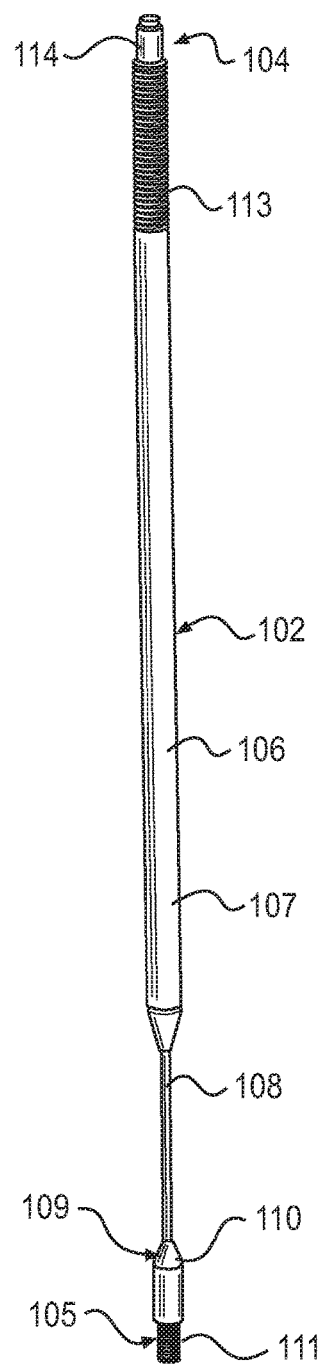
Figure 16C:
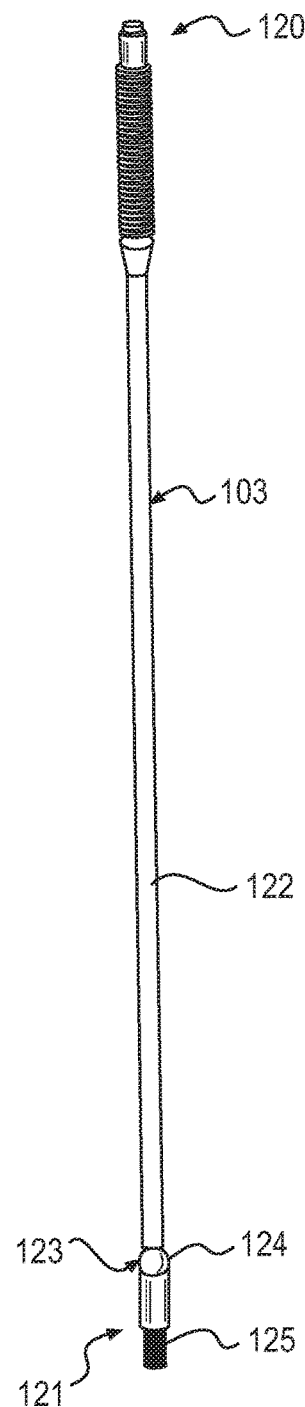

FIG. 16a,b,c shows an elevation view of support member 41 in isolation and two alternative configurations embodied in support members 102 and 103. Support member 102 of FIG. 16b has a proximal end 104, distal end 105 and therebetween a body 106. Body 106 as shown has a wide region 107 and a narrow region 108. Wide region 107 has a greater diameter in comparison to region 45 of support member 41. Narrow region 108 terminates in formation 109 which comprises a flared portion 110 and threaded shaft 111. Narrow region 108 has in built bending flexibility to allow movement of wide region 107 when adjustment is required. In use, threaded shaft 111 engages a screw (not shown). At proximal end 104 is a threaded region 113 and hexagonal formation 114 which receives and retains wing nut 54. Support member 102 is inserted using insertion tool 55 as previously described. Support member has a stronger spine at wide region 107.

Figure 17:
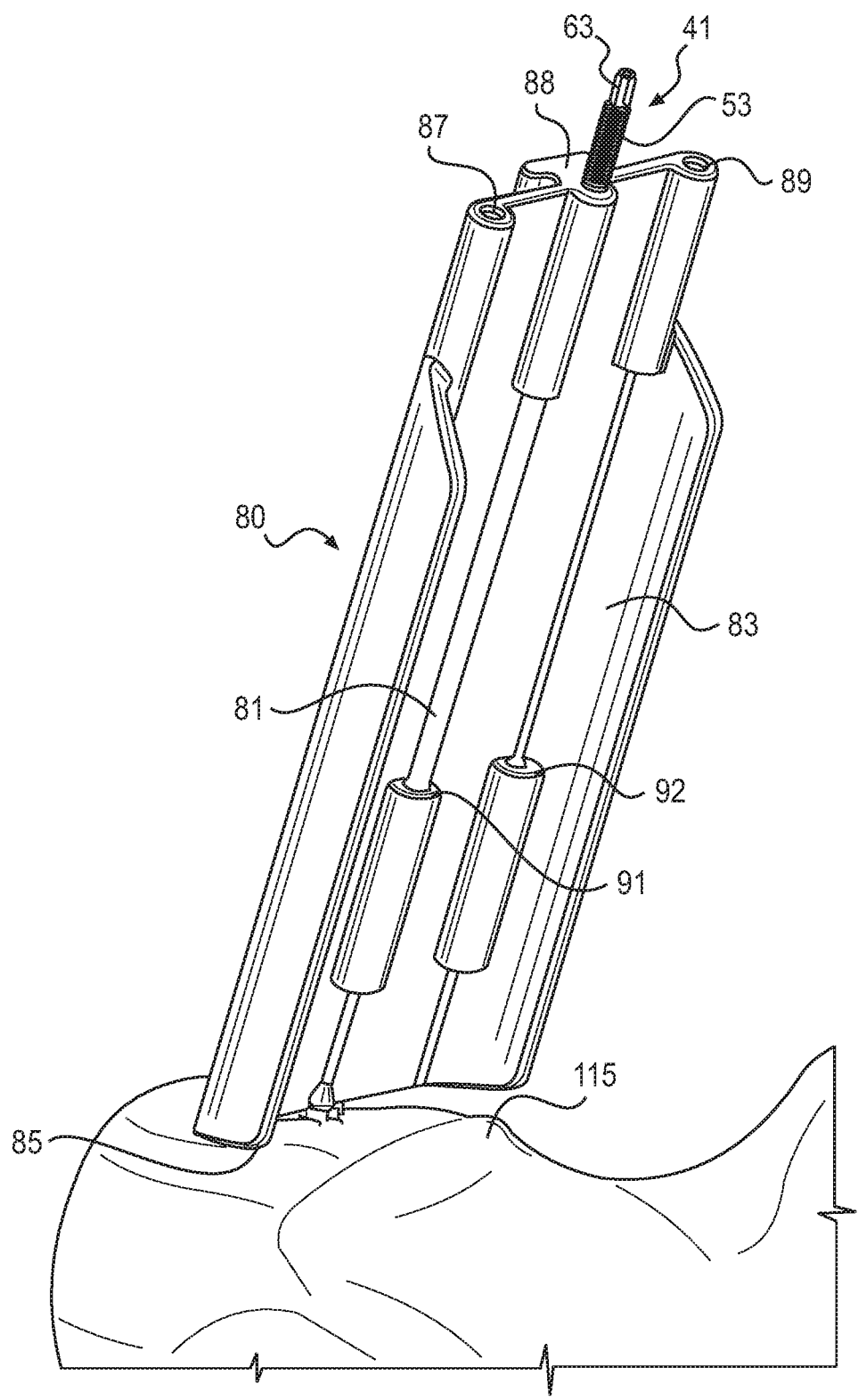
FIG. 17 shows a perspective view of an alternative retractor blade engaged with the support member.

Support member 103 has a proximal end 120 and distal end 121 and therebetween a body 122. Body 122 has the predominantly the same along its length. Body 122 terminates in formation 123 which comprises a flared portion 124 and threaded shaft 125. Body 122 has in built bending flexibility to allow bending when adjustment is required. A straight wire with threads on proximal and distal ends is also contemplated. FIG. 17 shows with corresponding numbering a perspective view of an alternative retractor blade 80 described with reference to FIG. 7 engaged with the support member 41 anchored in vertebrae 115.

Figure 18:
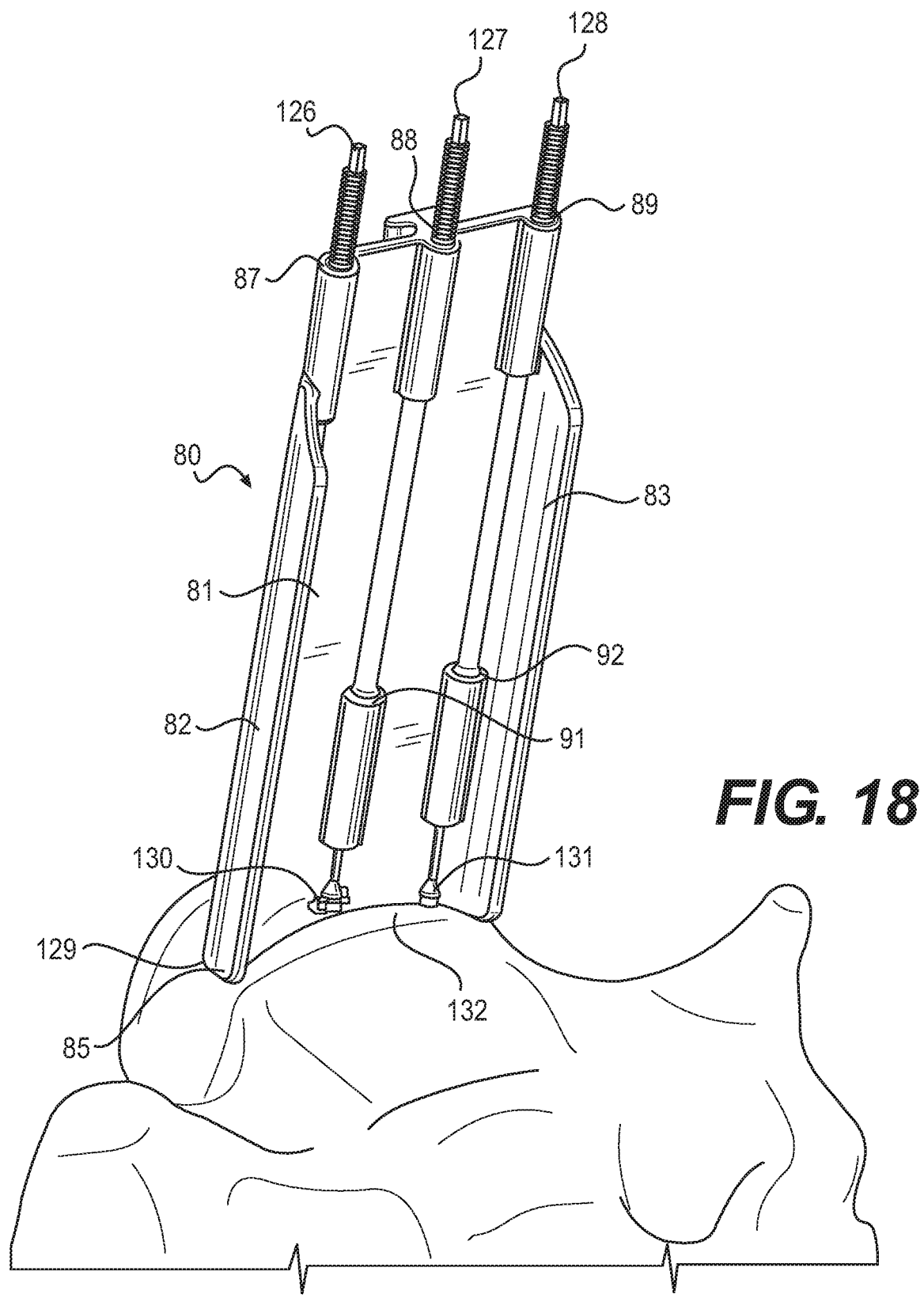
FIG. 18 shows the blade of FIG. 17 with three point anchorage using three separate support members.

FIG. 18 shows the blade 80 of FIG. 17 with three point anchorage using three separate support members 126, 127 and 128. This arrangement increases retraction strength, but maintains the capacity for blade rotation relative to the anchor points 129, 130 and 131 in vertebrae 132.

Figure 19:
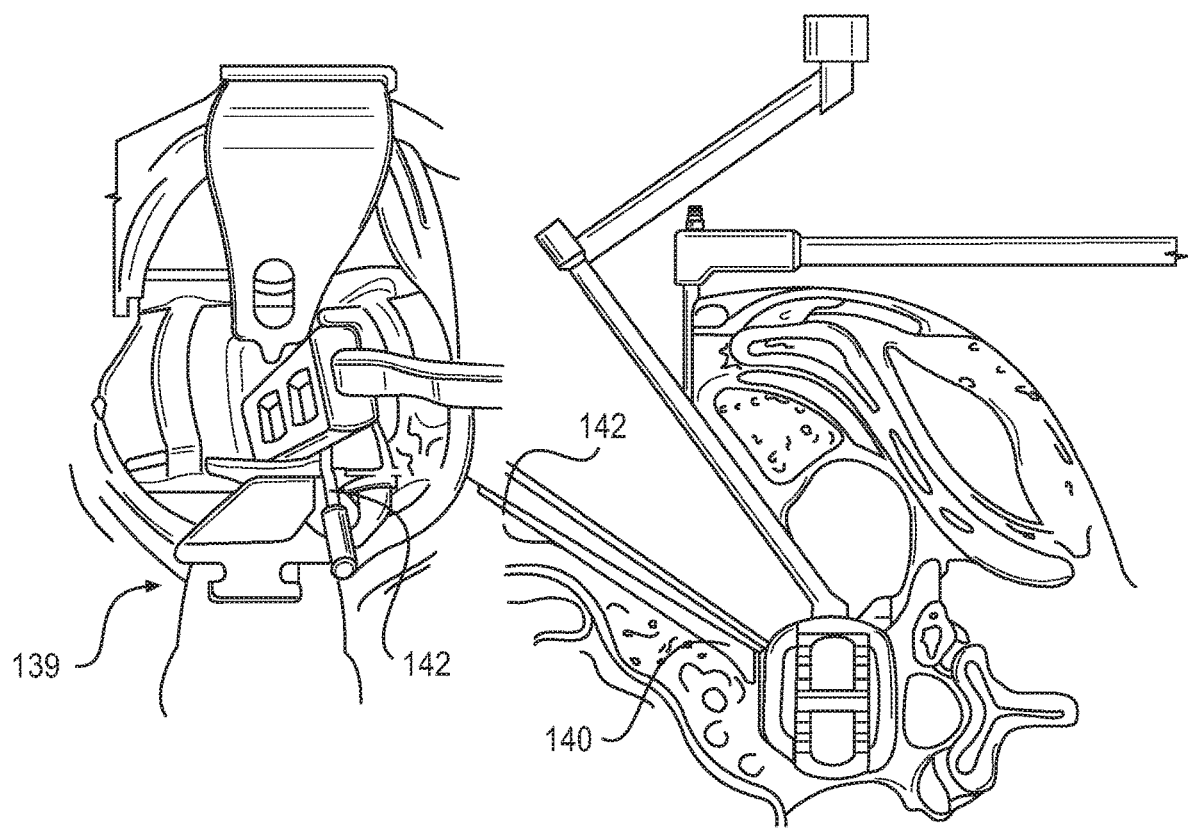
FIG. 19 shows an illustration of a soft tissue anchored retractor assembly showing a hook formation used during atp spinal fusion surgery.

FIG. 19 shows an illustration of a soft tissue anchored retractor assembly 139 showing hook 140 used during atp spinal fusion surgery. The assembly according to the invention provides an alternative to the use of a known L shaped retractor blade for a flat blade and allows replacement of screw fixation with a hook on the end of a support member 142 which engages the ALL and annulus, thereby holding the retractor onto the disc. Although shown at the edge of the disc, a central position on the disc may be adopted.

Figure 20:
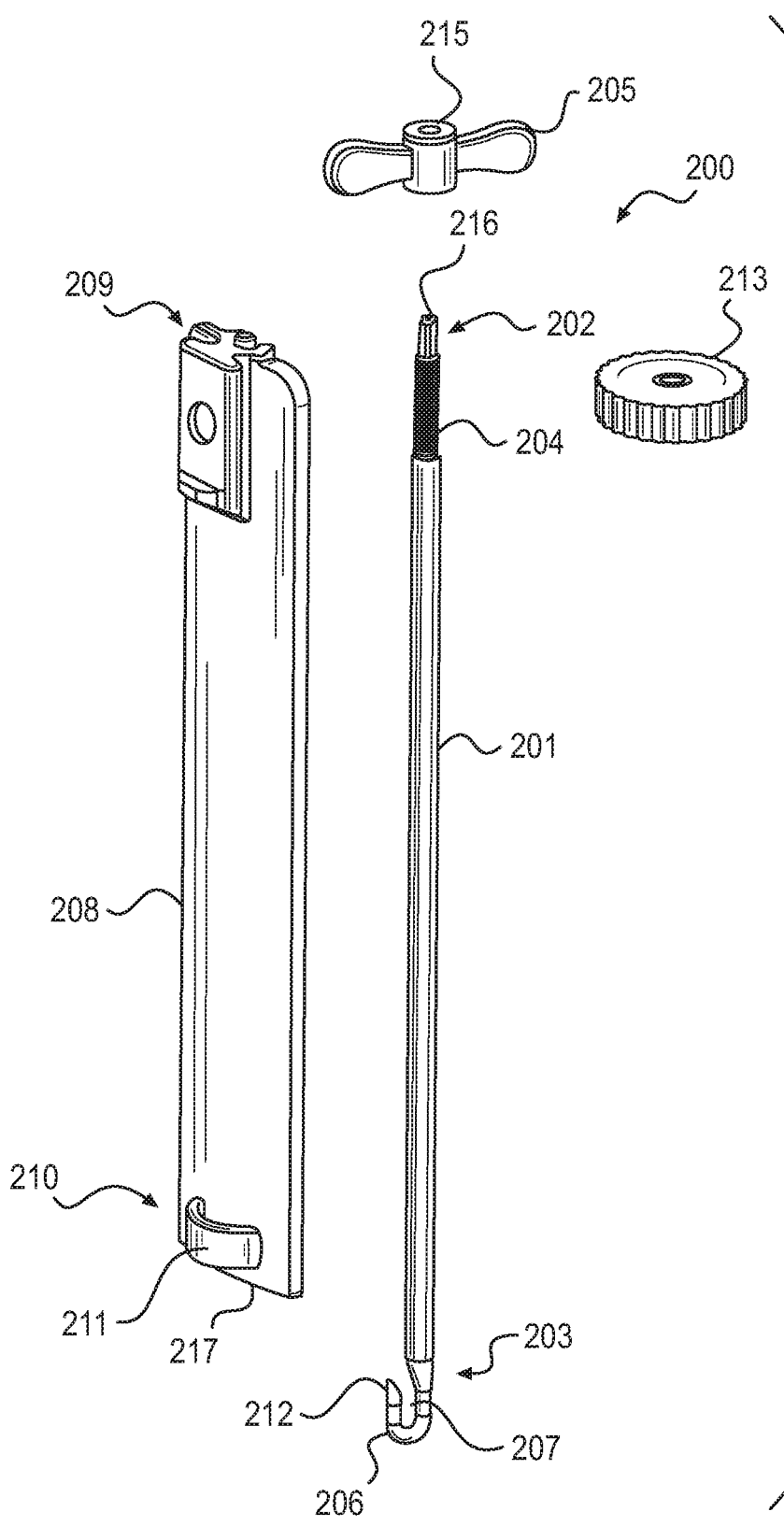
FIG. 20 shows an exploded view of a retraction assembly according to a preferred embodiment including a wing nut and coin nut.

FIG. 20 shows an exploded view of a retraction assembly 200 according to another embodiment. Assembly 200 includes support member 201 having a first end 202 and second (distal) end 203. First end 203 has a threaded region 204 which when in use receives and retains thereon a coin nut 213. A wing nut 205 includes a female recess 215 which engages corresponding male hexagonal formation 216. Second end 203 terminates in a hook like formation 206 which defines a recess 207. Assembly 200 further comprises a retractor blade 208 having a first end 209 and a second end 210. First/proximal end 209 receives proximal end 202 of support member 201. Second end 210 includes a saddle 211 which accommodates formation 206 providing a cover pocket for sharp point 212 of hook formation 206 when the hook formation has been withdrawn from engagement with a ligament. Assembly 200 further comprises a coin nut 213 which in use, engages threaded region 204 and locks support member 201 against first end 209 of blade 208. Wing nut 205 allows adjustment of the orientation of support member 201 by rotation.

Figure 21:
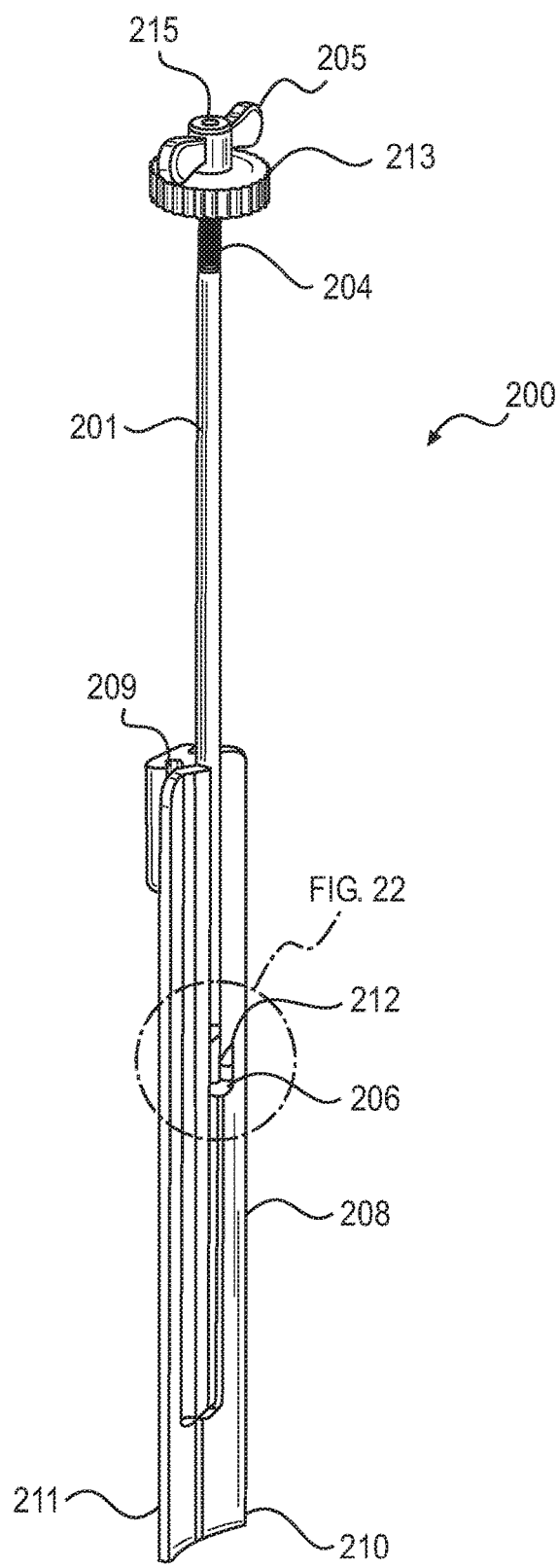
FIG. 21 shows a partially assembled view of the assembly of FIG. 20.
Figure 22:
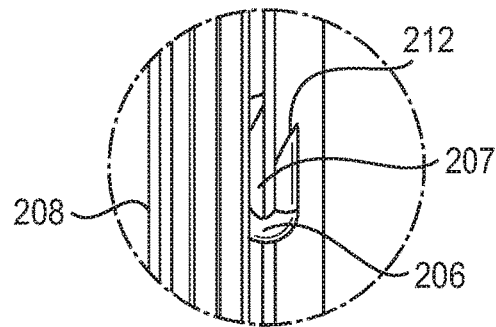
FIG. 22 shows an enlarged view of the distal end hook formation of FIG. 20.

FIG. 21 shows with corresponding numbering a partially assembled view of the assembly of FIG. 20. In this case wing nut 205 is shown mounted on formation 216 (obscured) and coin nut 213 is mounted on threaded region 204. FIG. 22 shows an enlarged view of the distal end hook formation of FIG. 20.

Figure 23:
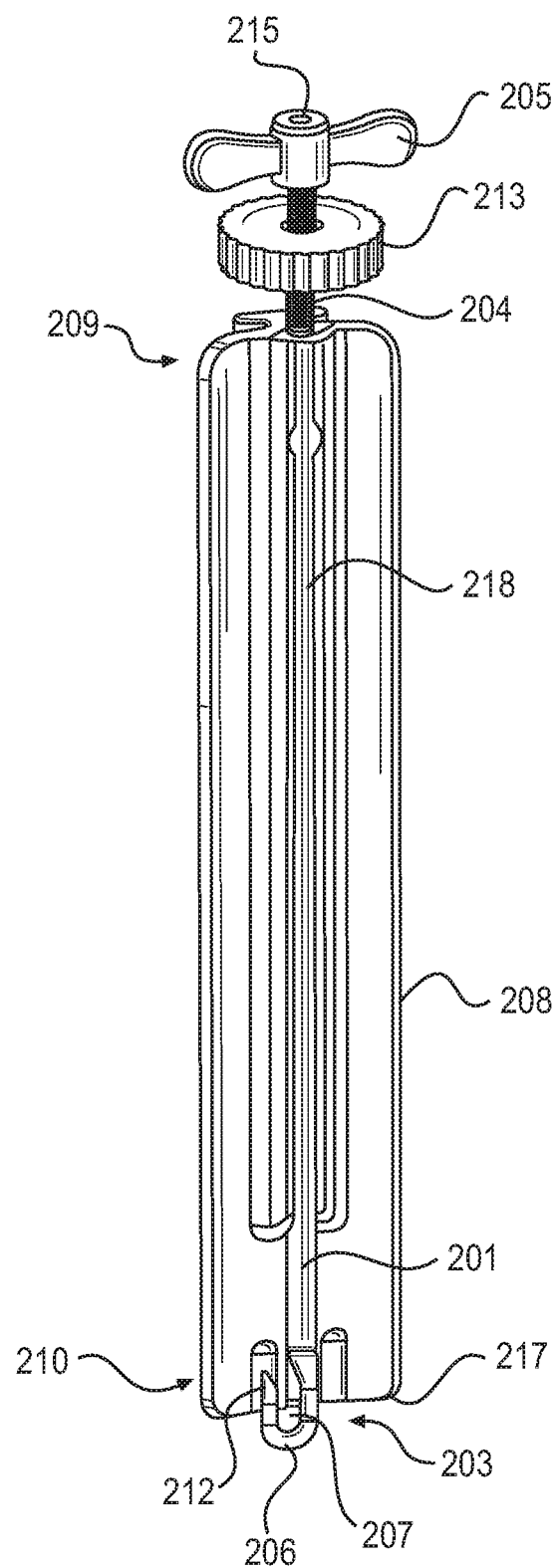
FIG. 23 shows the assembly of FIG. 20 fully assembled.

FIG. 23 shows with corresponding numbering the assembly of FIG. 20 fully assembled. In this case wing nut 205 is shown mounted on formation 216 (obscured) and coin nut 213 is mounted on threaded region 204. Coin nut 213 can be vertically adjusted along thread 204 thereby adjusting the vertical position of hook 206 relative to end 210 of blade 208. Wing nut 205 allows support member 201 to be rotated 360 degrees such that it may be operated at the rear or front of blade 208. Support member 201 is rotatable within recess 218 of blade 208 and may also undergo vertical adjustment by use of coin nut 213. End 210 of blade 208 terminates in a flat edge 217. This arrangement allows hook 206 when in use to compress the ligament (ALL) against the distal edge 217 of blade 208 when it is withdrawn with the hook 206 facing backwards. This ability to compress, provides additional fixation. In the earlier embodiments described with reference to FIGS. 1-19, the end 67 of blade 65 is curved or radiused rearward allowing the hook to operate forward of the blade. In the embodiment of FIGS. 20-23 the straight blade edge 217 allows that hook to be used forward and backwards relative to the blade. Another facility when hook 206 faces forwards is that coin locking nut 212 can draw support member 201 along recess 218 of blade 208 and release from a ligament by tearing to release the hook.

Figure 24:
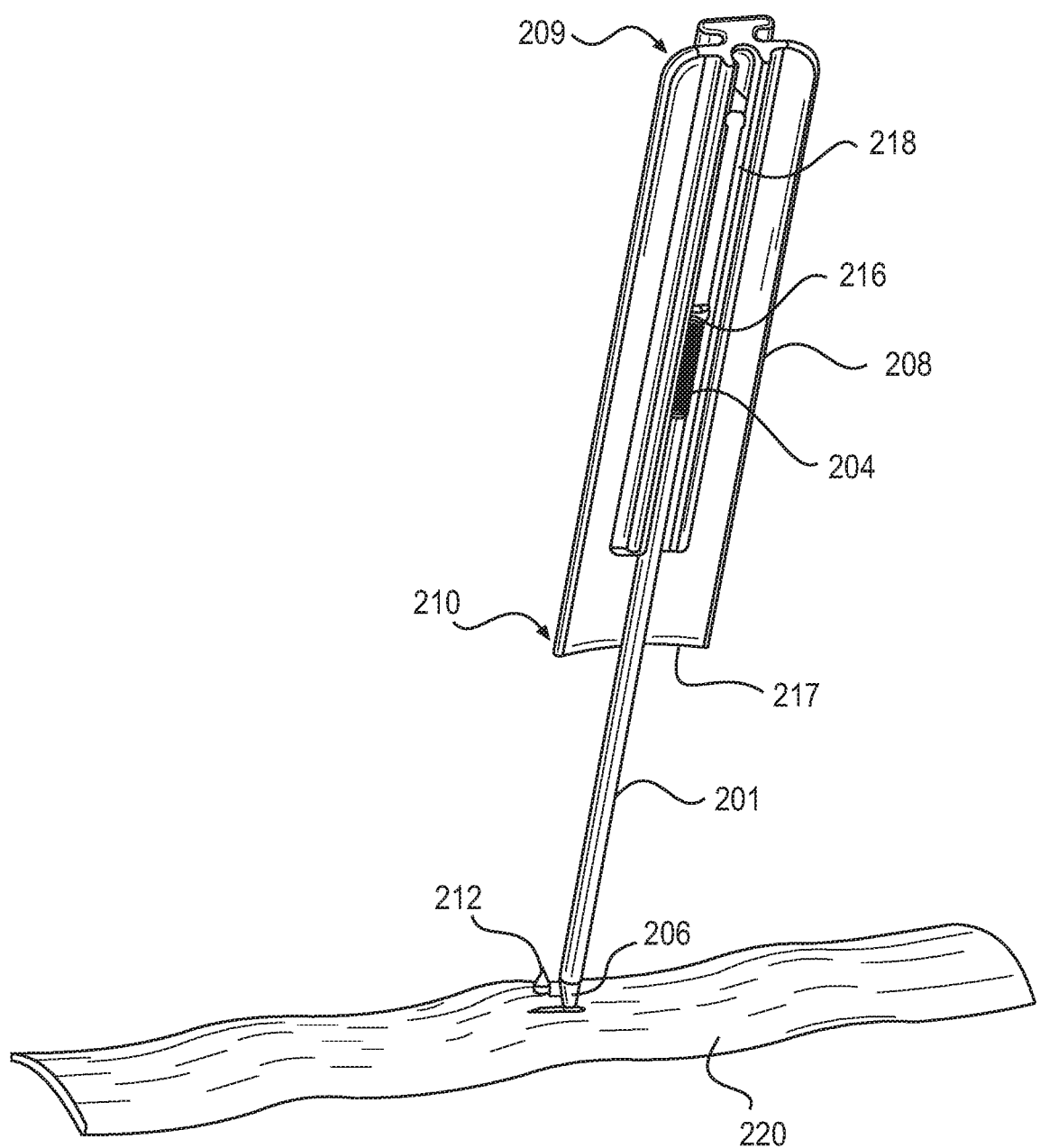
FIG. 24 shows the assembly with hook of support member engaging a soft tissue.
Figure 25:
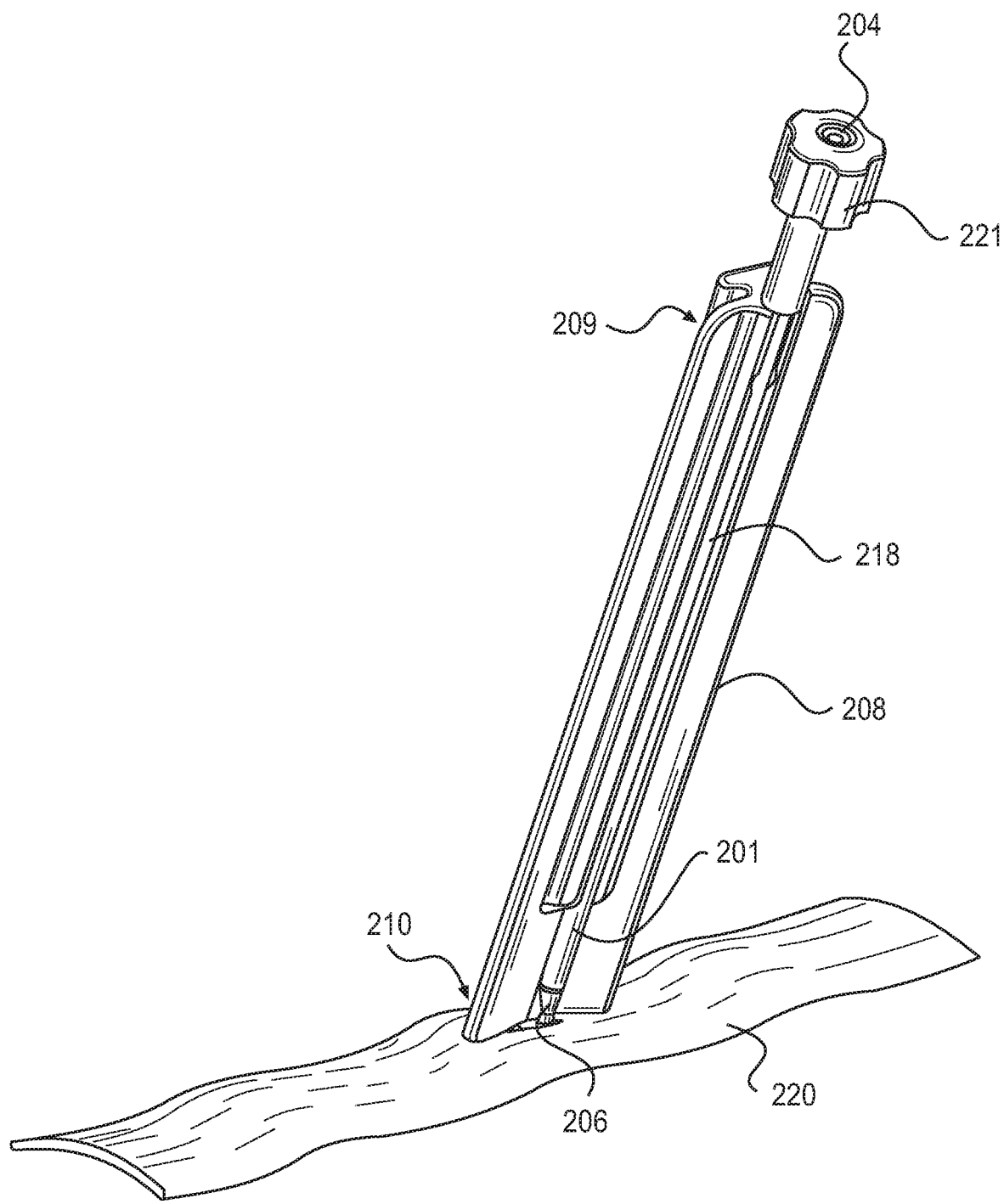
FIG. 25 shows a perspective view of the retraction assembly ac cording to an alternative embodiment engaged with soft tissue and including an alternative locking nut.

FIG. 24 shows with corresponding numbering, the assembly 200 with hook 206 of support member 201 engaging a soft tissue ligament 220. FIG. 25 shows a perspective view of the retraction assembly according to an alternative embodiment engaged with soft tissue ligament 220 and including an alternative clamping/locking nut 221. Nut 221 includes a threaded sleeve which engages thread 204 (obscured) of support member 201. This enables locking of support member 201 against blade 208 and allows hook 206 to be drawn up against ligament 220.

Figure 26:
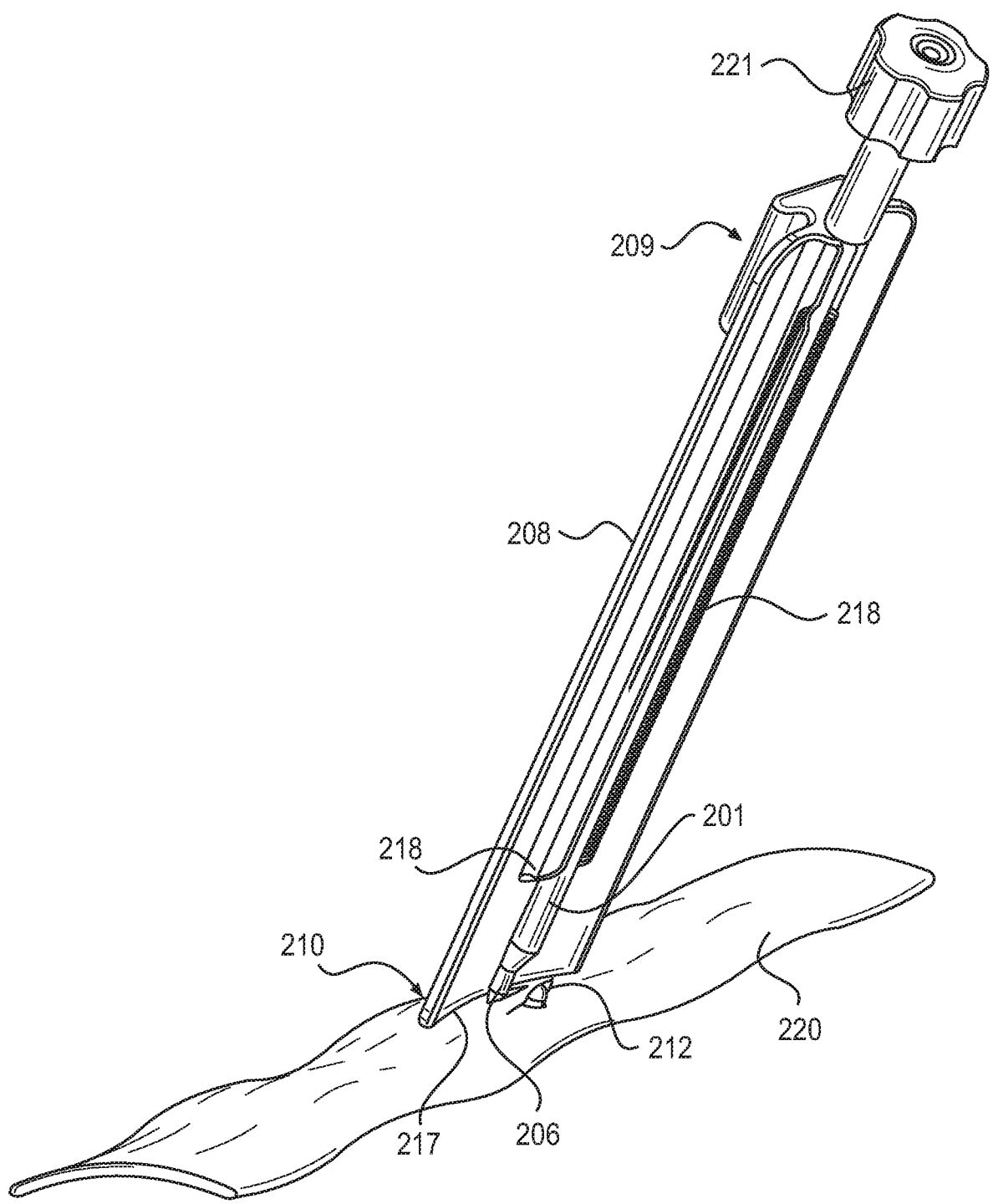
FIG. 26 shows the assembly of FIG. 25 with distal end hook penetrating through soft tissue.

FIG. 26 shows the assembly of FIG. 25 with distal end hook 206 penetrating through soft tissue 220 and point 212 emerging therethrough.

Figures 27A, 27B:
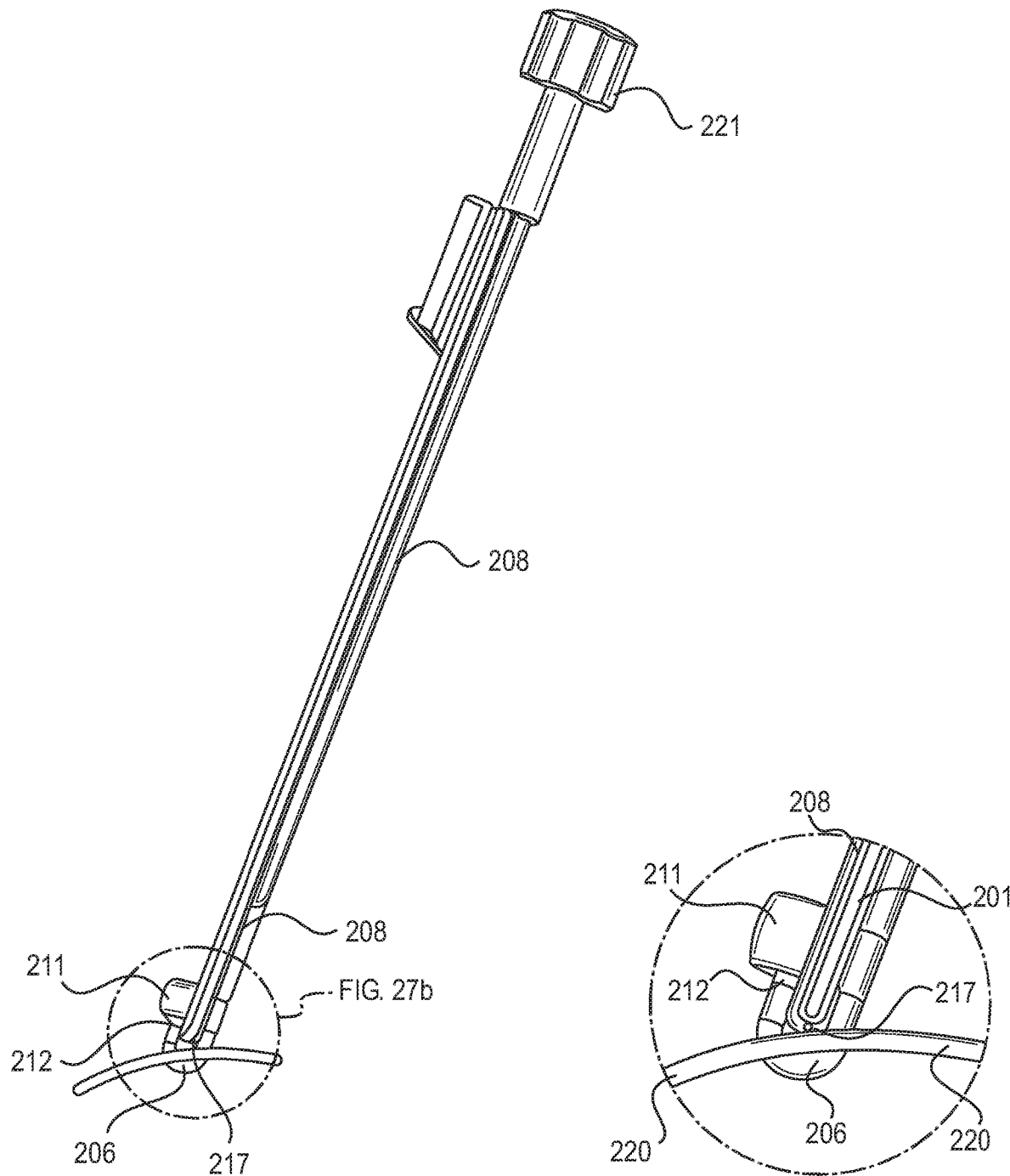
FIGS. 27a & b show a side elevation of the assembly and an enlarged view of the view of the distal end hook
Figure 28:
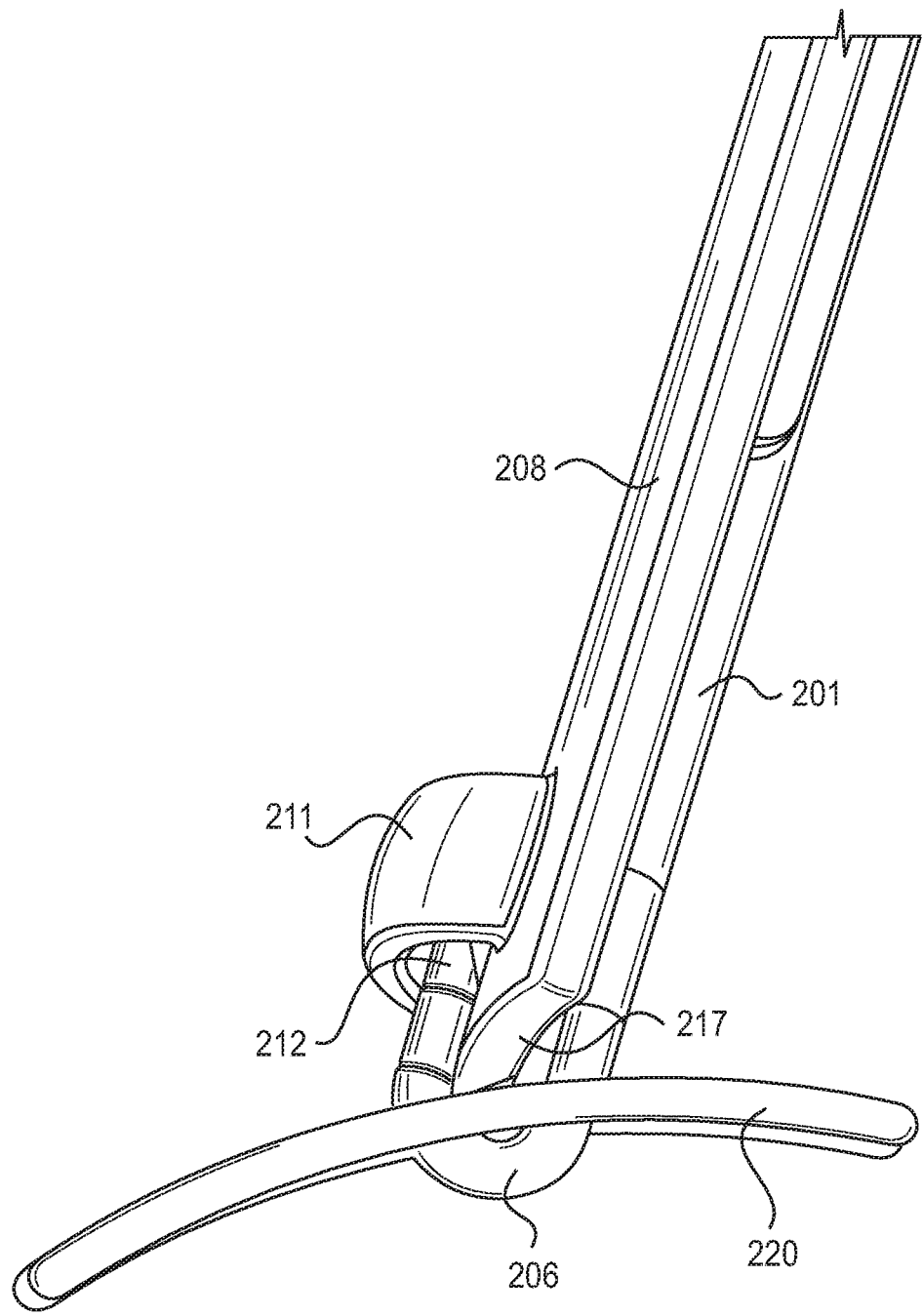
FIG. 28 shows an enlarged perspective view of the distal end of the assembly
Figure 29:
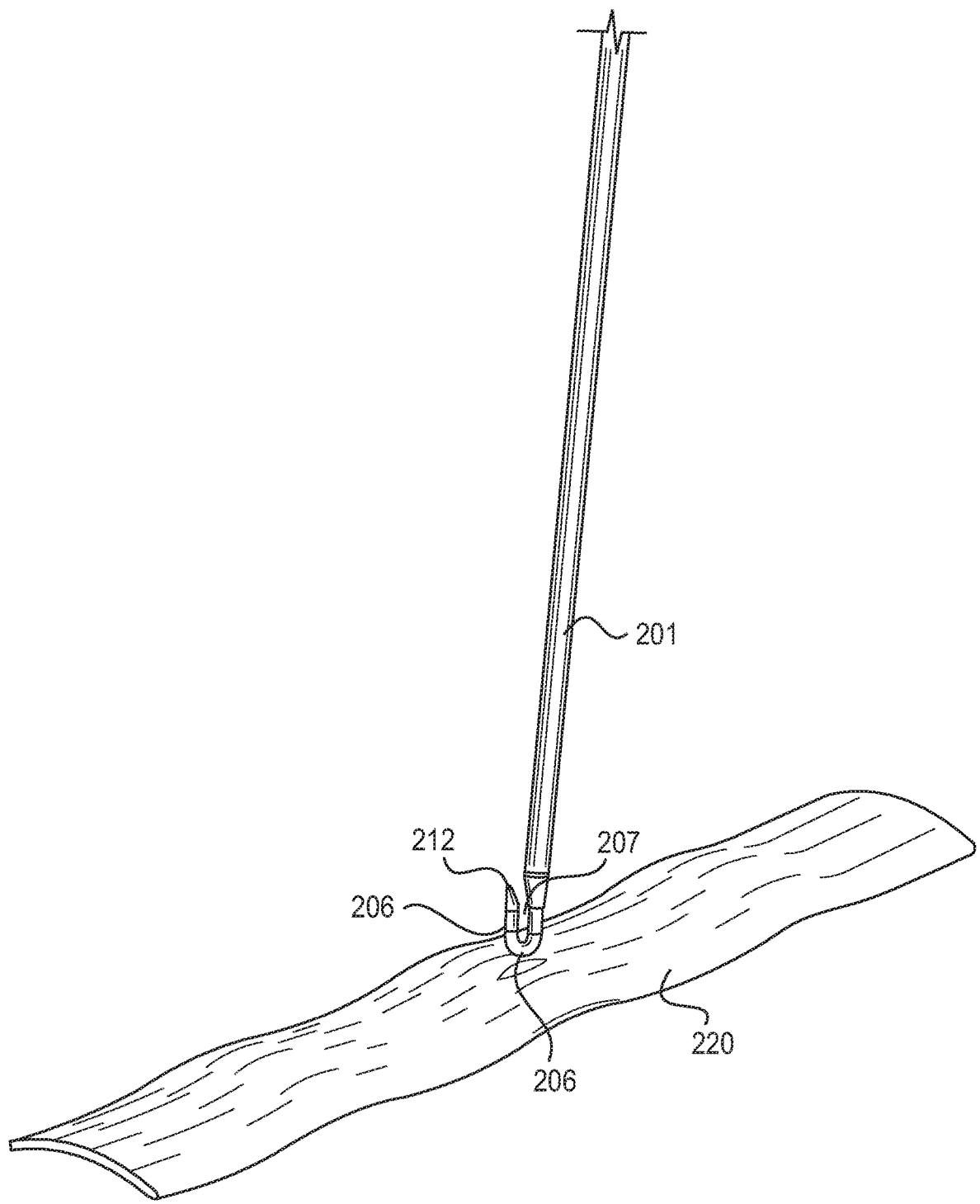
FIG. 29 shows the support member and distal hook in isolation and engaged with soft tissue.
Figure 30:
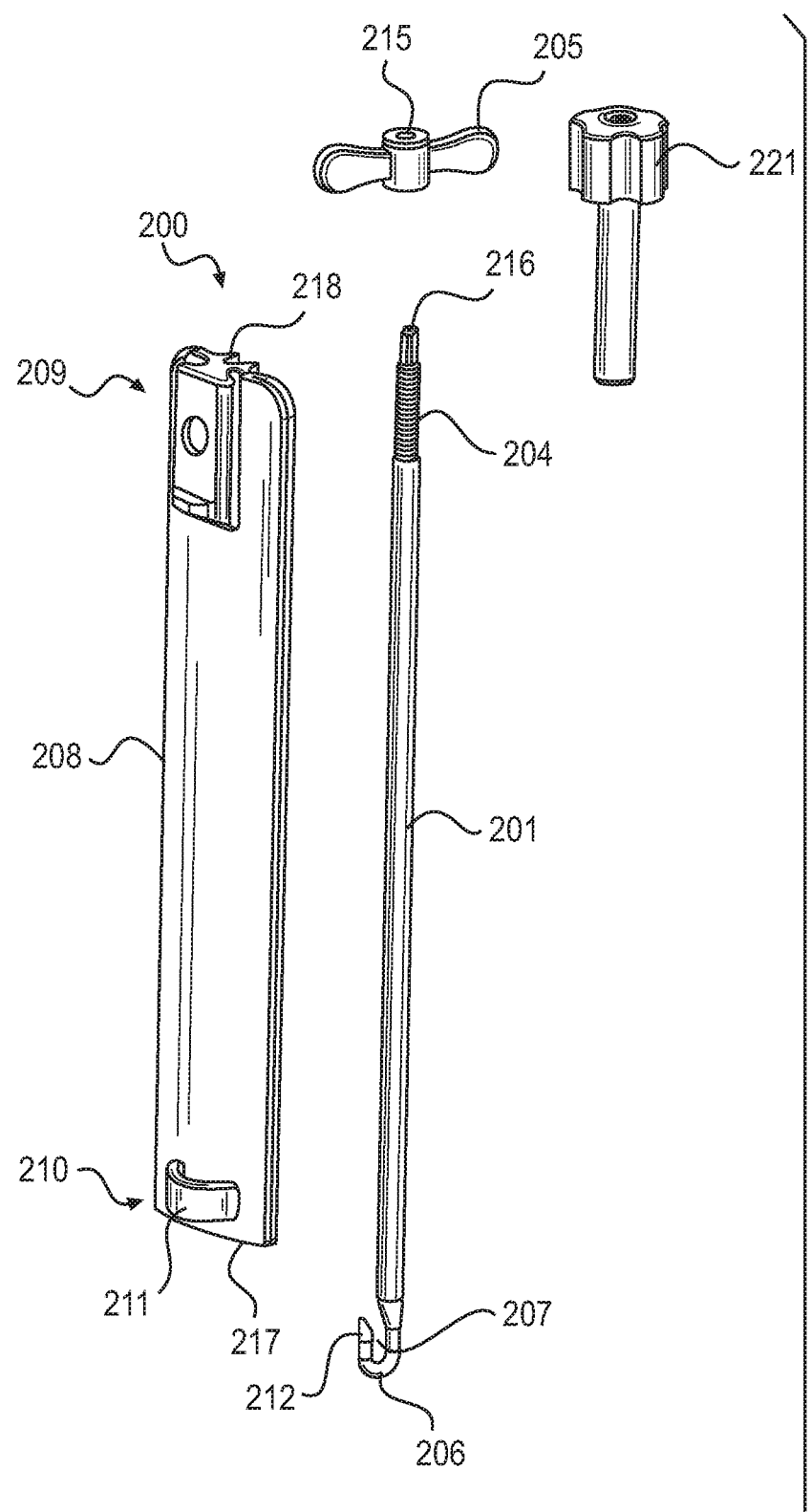
FIG. 30 shows an exploded view of the retraction assembly with a wing nut and locking nut.

FIGS. 27a & b shows a side elevation of the assembly of FIG. 26 and an enlarged view (FIG. 27b) of the view of the distal end hook 206. In the arrangement shown, hook 206 is shown engaging soft tissue 220 but facing rearwards so that point 212 locates inside saddle cover 211. In this case ligament 220 is sandwiched between hook 206 and end 217 of blade 208. FIG. 28 shows with corresponding numbering an enlarged perspective view of the distal end of the assembly 200 of FIG. 27b. FIG. 29 shows the support member 201 and distal hook 206 in isolation and engaged with soft tissue 220. FIG. 30 shows an exploded view of the retraction assembly 200 with wing nut 205 and alternative locking/clamping nut 221 isolated from the assembly.

Figure 31:
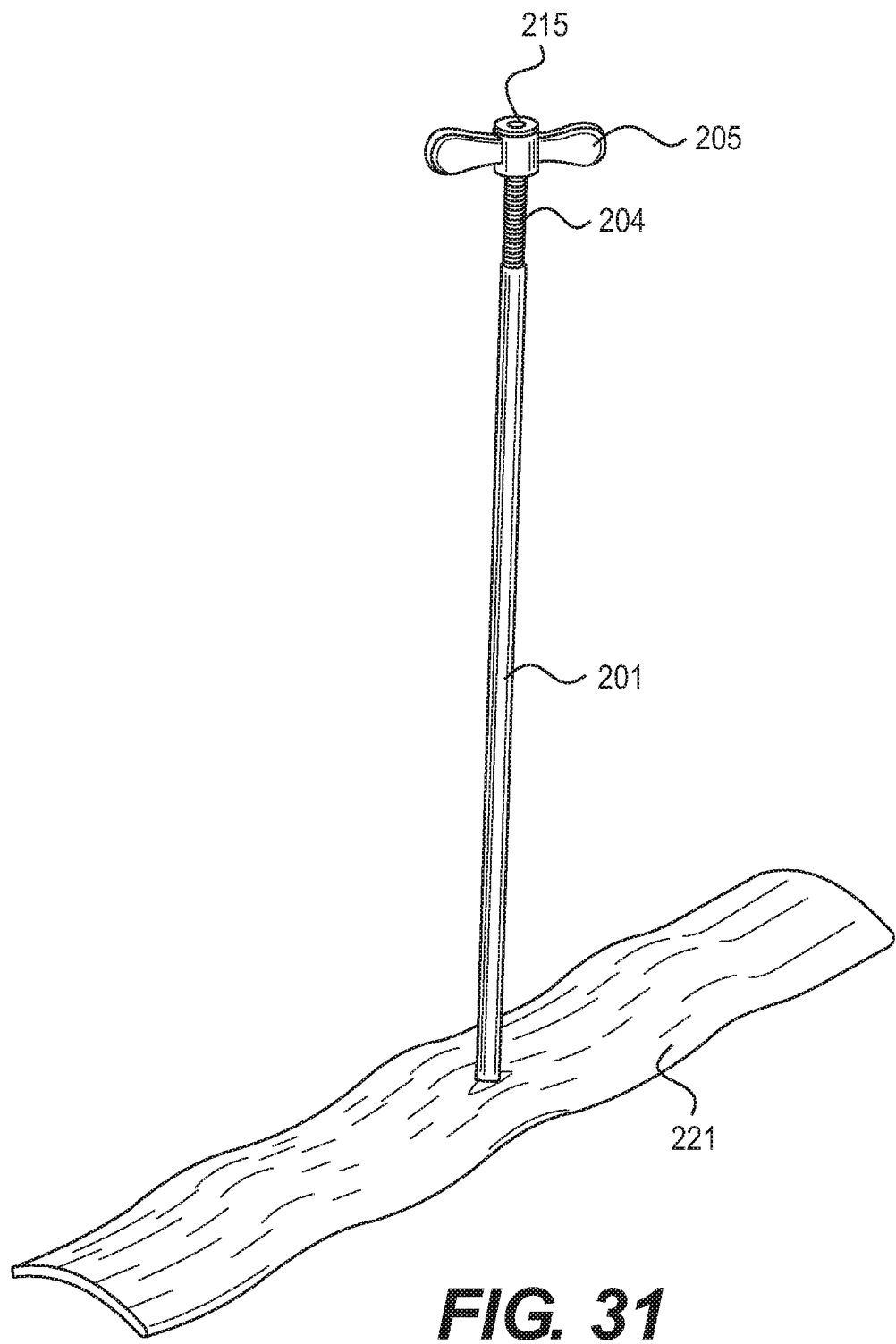
FIG. 31 shows the support member of the assembly of FIG. 30 engaging soft tissue and including the wing nut.
Figure 32:
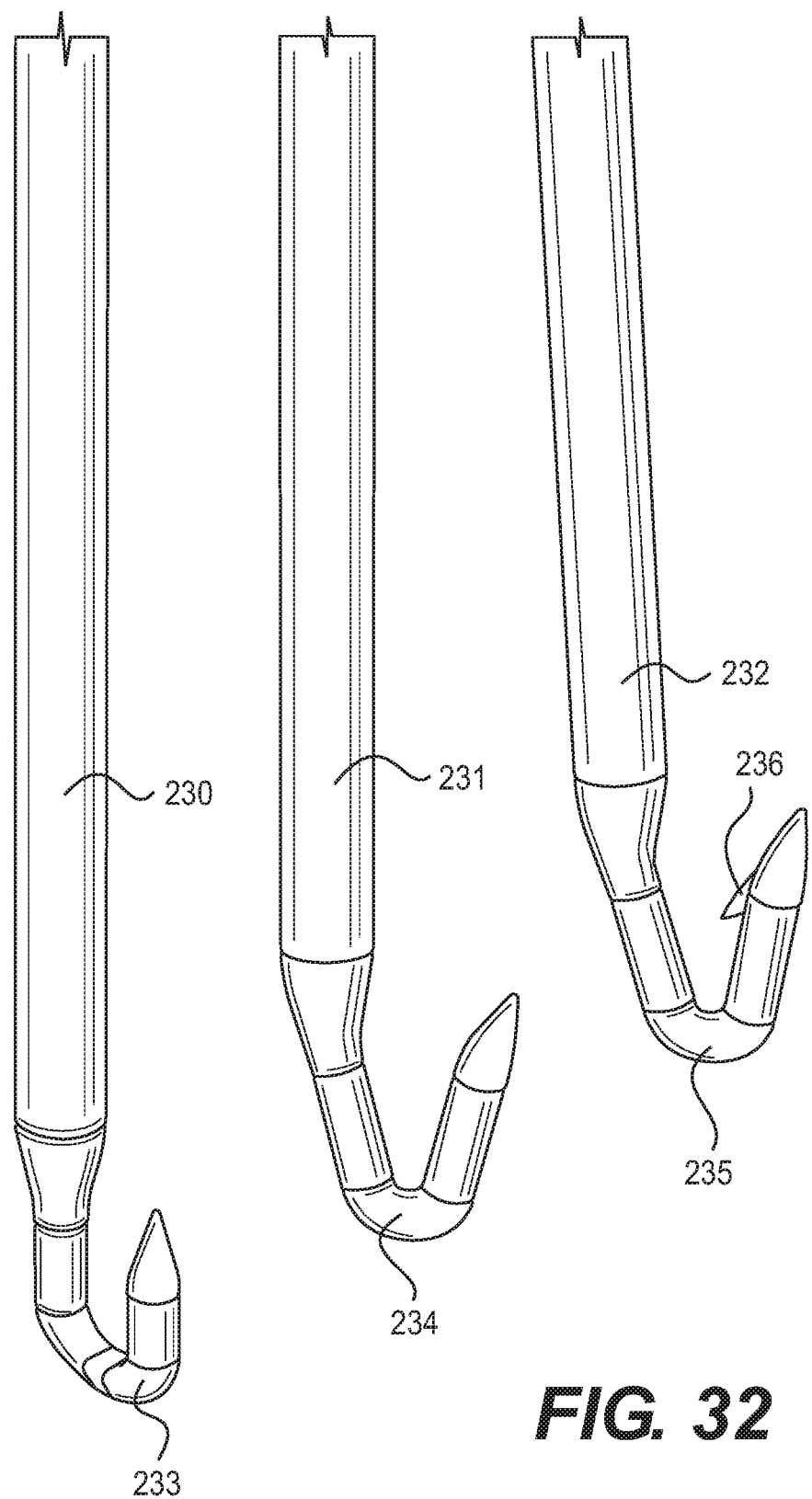
FIG. 32 shows the shape and configuration of contemplated hook geometries.

FIG. 31 shows the support member 201 of the assembly 200 isolated and engaging soft tissue 221. Wing nut 205 is shown engaging formation 216 (obscured) via recess 215 enabling a user to rotate support member through 360 degrees. FIG. 32 shows the shape and configuration of three support members 230, 231 and 232 respectively terminating in hook formations 233, 234 and 235. Hook 233 is closer to U shaped whereas hooks 234 and 235 are V shaped. Hook 235 includes a barb 236 which acts in a similar manner to a barbed hook by resisting unwanted withdrawal of soft tissue.

Figure 33:
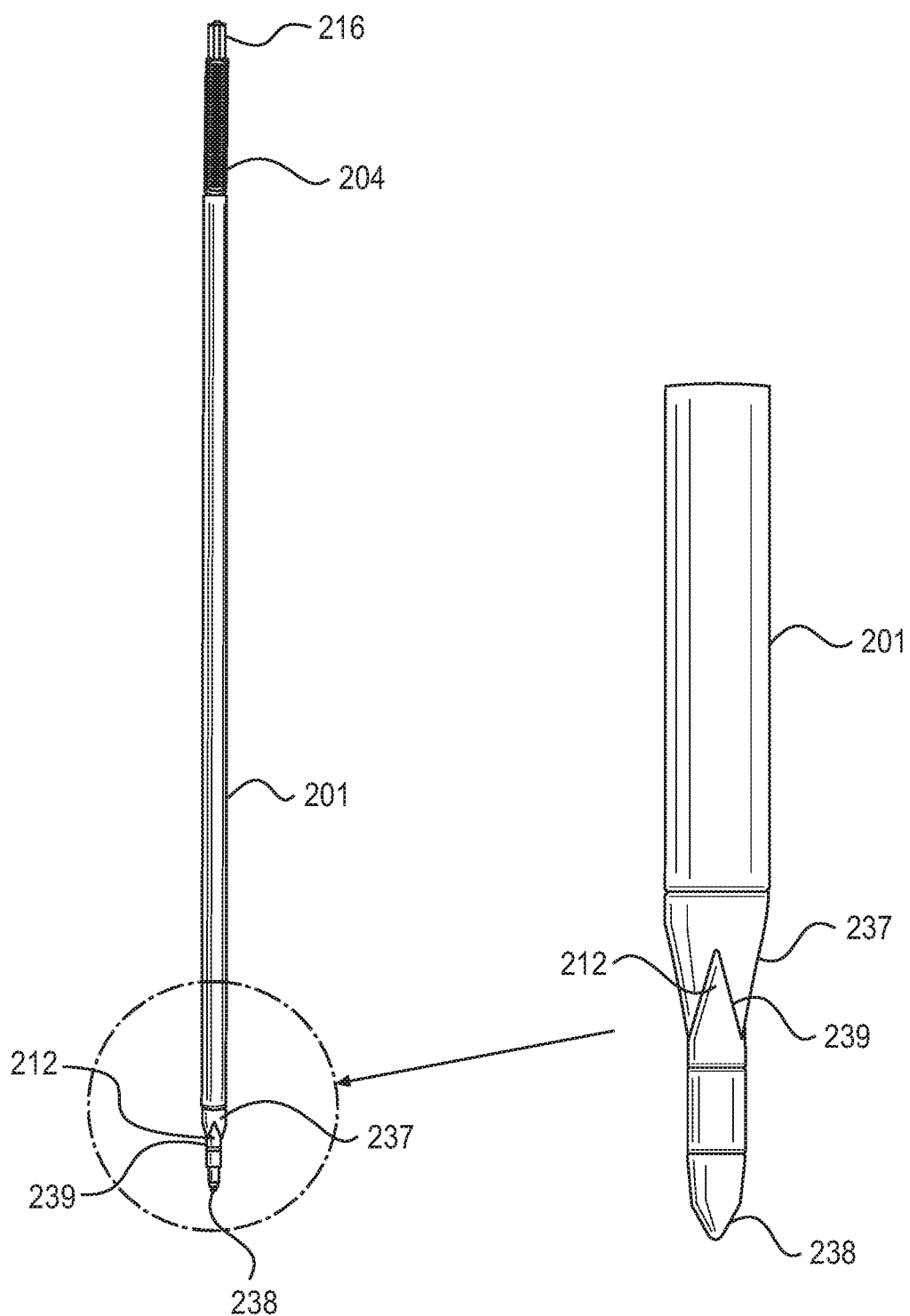
FIG. 33 shows a front elevation of the hook indicating tapering regions.

FIG. 33 shows a front elevation of the support member 201 and hook 206. As seen in the enlarged view, hook 206 includes tapered regions. A first reducing tapered region 237 reduces the diameter of support member 201. A second taper 238 is located at the bottom of hook 206. A third taper 239 produces sharp point 212.

Figure 34A:
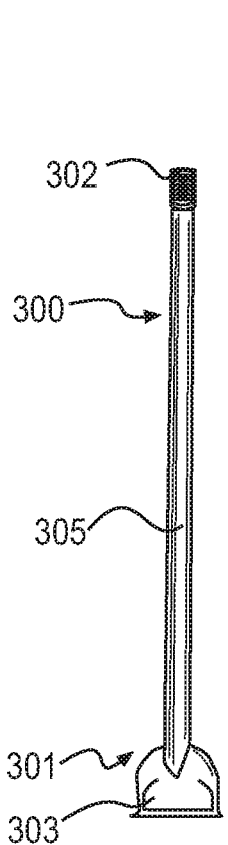
Figure 34B:
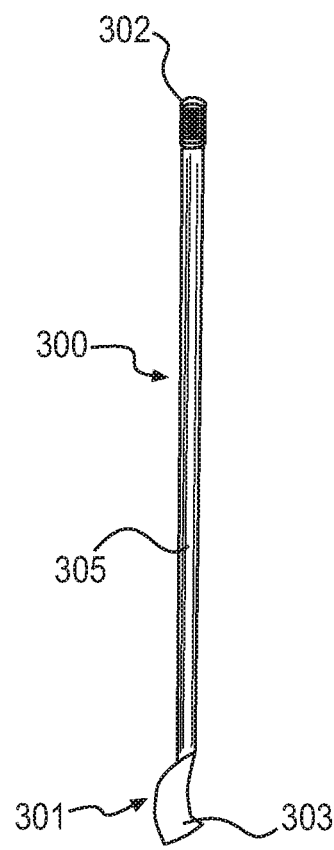
Figure 34C:
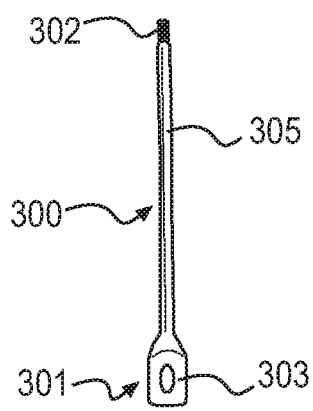
Figure 34D:
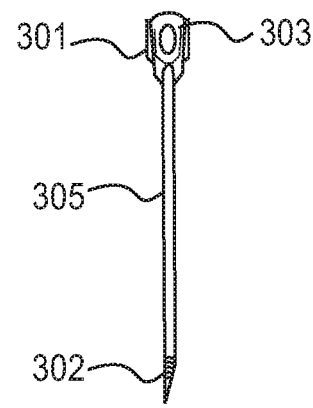

FIG. 34a-f shows a support member 300 according to various views and having alternative geometry and a flexible distal hinge. Support member 300 is adapted to co operate with a retractor blade as described earlier (see FIGS. 5 and 6 for instance). FIG. 34a shows a front elevation view of support member 300 having a distal end 301 and proximal end 302. Support member 300 is analogous to the embodiment of FIGS. 5 and 6 which was described with reference to a hinge arrangement 28, except that the support member 300 is manufactured from a plastics material which has elastic flexibility. At distal end 301 there is provided a formation 303 which is cable of receiving an anchor (not shown) which locates in bone. This anchorage allows the body 305 of support member 300 to undergo flexure relative to the anchorage as formation 303 elastically deforms as a hinge. FIG. 34b shows a side elevation of support member 300. FIG. 34c shows a plan view of the support member 300. FIG. 34d shows a sectional view taken at B-B through formation 303. FIG. 34e shows another elevation view of support member 300 and FIG. 34f shows an enlarged view of proximal end thread. Preferably support member 300 will fall within a length range of 100-150 mm although alternative lengths are contemplated to engage different sized retractor blades.

Variations in the retractor assembly may be made to accommodate different variations in engagement to vertebrae. For instance the length, width and relative heights of horizontal and vertical sections, may vary to accommodate, different locations in the spine and different types of procedures. It will be further recognised by persons skilled in the art that numerous variations and modifications may be made to the invention without departing from the overall spirit and scope of the invention broadly described herein.

The claims defining the invention are as follows:

1. A surgical retractor blade assembly for retraction of soft tissue during surgery, the assembly comprising:
    at least one support member having a proximal end and a distal end,
    a retractor blade having a distal end and a proximal end and adapted to detachably engage the at least one support member,
    the distal end of each support member including a formation which enables anchorage of the distal end of the support member to a bone anchor of a patient and freedom for the proximal end of the support member and attached blade to undergo manually induced displacement in unison,
    wherein the retractor blade includes a medial passage which retains thereon one said at least one support member, the at least one support member lockable against the retractor blade at its proximal end; and
    the distal end of the support member including a threaded region which detachably engages the bone anchorage, the distal end of the support member further comprising a region of flexibility which allows the retractor blade and support member to swivel about an axis through the anchorage.

2. The retractor blade assembly according to claim 1 wherein there is one said support member and the bone anchor includes a distal male thread which is fixed to the bone and threaded recess which receives the threaded region of the distal end of the support member.

3. The retractor blade assembly according to claim 2 wherein the assembly further comprises a handle which engages the proximal end of the retractor blade, thereby enabling manual adjustment of the orientation and attitude of the retractor blade and support member.

4. The retractor blade assembly according to claim 3 wherein the assembly further comprises an insertion tool which concentrically engages the support member to enable torsional insertion of the distal threaded region of the support member into said bone anchorage.

5. The retractor blade assembly according to claim 4 wherein the support member is pivotally adjustable relative to the bone anchorage.

6. The retractor blade assembly according to claim 5 wherein the region of flexibility is elastic and is created by a narrowing at or near the distal end of the support member.

7. The retraction assembly according to claim 6 wherein the proximal end of the support member includes a threaded region and engages a sleeve in the retractor blade.

8. The retraction assembly according to claim 7 wherein the proximal end threaded region receives and retains a locking nut which secures the support member to the retractor blade, thereby preventing relative movement therebetween.

* * * * *